(12) United States Patent
Furman

(10) Patent No.: US 11,359,011 B2
(45) Date of Patent: Jun. 14, 2022

(54) TREATMENT AND PREVENTION OF CARDIOVASCULAR DISEASE

(71) Applicant: Edifice Health, Inc., San Mateo, CA (US)

(72) Inventor: David Furman, San Mateo, CA (US)

(73) Assignee: Edifice Health, Inc., San Mateo, CA (US)

( * ) Notice: Subject to any disclaimer, the term of this patent is extended or adjusted under 35 U.S.C. 154(b) by 0 days.

(21) Appl. No.: 16/987,010

(22) Filed: Aug. 6, 2020

(65) Prior Publication Data

US 2021/0040195 A1 Feb. 11, 2021

Related U.S. Application Data

(60) Provisional application No. 62/884,108, filed on Aug. 7, 2019.

(51) Int. Cl.

| | | |
|---|---|---|
| *C07K 16/24* | (2006.01) | |
| *C07K 16/28* | (2006.01) | |
| *A61K 33/36* | (2006.01) | |
| *A61K 31/285* | (2006.01) | |
| *A61K 38/18* | (2006.01) | |
| *A61K 31/4745* | (2006.01) | |
| *A61K 31/05* | (2006.01) | |
| *A61K 38/20* | (2006.01) | |
| *A61K 33/04* | (2006.01) | |

(52) U.S. Cl.
CPC .............. *C07K 16/24* (2013.01); *A61K 31/05* (2013.01); *A61K 31/285* (2013.01); *A61K 31/4745* (2013.01); *A61K 33/04* (2013.01); *A61K 33/36* (2013.01); *A61K 38/1841* (2013.01); *A61K 38/2006* (2013.01); *C07K 16/2866* (2013.01)

(58) Field of Classification Search
None
See application file for complete search history.

(56) References Cited

U.S. PATENT DOCUMENTS

| | | | | |
|---|---|---|---|---|
| 8,318,170 | B2 * | 11/2012 | Lillard | A61P 1/00 424/145.1 |
| 2003/0109420 | A1 * | 6/2003 | Valkirs | G01N 33/6887 435/7.1 |
| 2006/0104941 | A1 * | 5/2006 | Ridker | A61K 31/40 424/78.12 |
| 2009/0042817 | A1 | 2/2009 | Heger et al. | |
| 2009/0155827 | A1 * | 6/2009 | Zeiher | G01N 33/6893 435/15 |
| 2009/0274660 | A1 | 11/2009 | Girsh | |
| 2011/0059089 | A1 | 3/2011 | Swagemakers et al. | |
| 2012/0021414 | A1 | 1/2012 | Shen-Orr et al. | |
| 2012/0122717 | A1 | 5/2012 | Satyaraj et al. | |
| 2012/0134929 | A1 | 5/2012 | McGrath et al. | |
| 2014/0031643 | A1 | 1/2014 | Pacemakers | |
| 2015/0126408 | A1 | 5/2015 | Link et al. | |
| 2017/0189447 | A1 | 7/2017 | Morris | |
| 2017/0234888 | A1 | 8/2017 | Defilippi et al. | |
| 2017/0249445 | A1 | 8/2017 | Devries et al. | |
| 2019/0024091 | A1 | 1/2019 | Wyss-Coray et al. | |
| 2019/0241669 | A1 | 8/2019 | Kuo et al. | |

FOREIGN PATENT DOCUMENTS

| | | |
|---|---|---|
| JP | 2004099471 | 4/2004 |
| WO | WO 2005/123101 | 12/2005 |
| WO | WO 2014/003742 | 1/2014 |
| WO | WO 2019/165145 | 8/2019 |
| WO | WO 2019/178296 | 9/2019 |

OTHER PUBLICATIONS

Ikonomidis, Ignatios, et al. "Increased proinflammatory cytokines in patients with chronic stable angina and their reduction by aspirin." Circulation 100.8 (1999): 793-798. (Year: 1999).*
Ma, Shuangtao et al. "E-selectin-targeting delivery of microRNAs by microparticles ameliorates endothelial inflammation and atherosclerosis." Scientific reports vol. 6 22910. Mar. 9, 2016, doi:10.1038/srep22910 (Year: 2016).*
Liang, Youfeng, et al. "Serum Monokine induced by gamma interferon is associated with severity of coronary artery disease." International heart journal 58.1 (2017): 24-29. (Year: 2017).*
Keefe, Anthony D et al. "Aptamers as therapeutics." Nature reviews. Drug discovery vol. 9,7 (2010): 537-50. doi:10.1038/nrd3141 (Year: 2010).*
Ding, Qiang et al. "CXCL9: evidence and contradictions for its role in tumor progression." Cancer medicine vol. 5, 11 (2016): 3246-3259. doi:10.1002/cam4.934 (Year: 2016).*
Corbera-Bellalta, Marc, et al. "Blocking interferon γ reduces expression of chemokines CXCL9, CXCL10 and CXCL11 and decreases macrophage infiltration in ex vivo cultured arteries from patients with giant cell arteritis." Annals of the rheumatic diseases 75.6 (2016): 1177-1186. (Year: 2016).*
Yun, James J et al. "The role of MIG/CXCL9 in cardiac allograft vasculopathy." The American journal of pathology vol. 161,4 (2002): 1307-13. doi:10.1016/S0002-9440(10)64407-0 (Year: 2002).*
Zhu, Liu, et al. "Molecular biomarkers in cardiac hypertrophy." Journal of cellular and molecular medicine 23.3 (2019): 1671-1677. (Year: 2019).*

(Continued)

*Primary Examiner* — Michael Szperka
*Assistant Examiner* — Lia E Taylor
(74) *Attorney, Agent, or Firm* — HelixIP LLP

(57) ABSTRACT

The methods and compositions described herein improve cardiovascular outcomes using measures related to systemic chronic inflammation (the inflammatory age—iAge, the cardiovascular age—cAge, and levels of certain markers) to stratify patients into low risk and high risk groups. The personalized immune proteome signature creates an individualized initial therapy to reduce cAge and to convert high risk patients into low risk patients. High risk patients can be converted to low risk patients by treating the patients to reduce their cAge, iAge and/or improve their CRS.

4 Claims, 7 Drawing Sheets

(56) References Cited

OTHER PUBLICATIONS

Swierczewska, Magdalena, Kang Choon Lee, and Seulki Lee. "What is the future of PEGylated therapies?." Expert opinion on emerging drugs 20.4 (2015): 531-536. (Year: 2015).*
Buss, Nicholas APS, et al. "Monoclonal antibody therapeutics: history and future." Current opinion in pharmacology 12.5 (2012): 615-622. (Year: 2012).*
Bandeen-Roche et al, Measuring systemic inflammatory regulation in older adults: evidence and utility, 2009, Rejuven. Res. vol. 12, pp. 403-410.
Alpert et al., A clinically meaningful metric of immune age derived from hiogh-dimensional longitudinal monitoring, 2019, Nature Med vol. 25, pp. 487-495.
Koentgeset al, SIRT3Deficiency impairs mitochondrial and conractile function in the heart, 2015, Basic Res Cardiol vol. 110, pp. 1-20.
Sayed et al., An inflammatory clock predicts multi-morbidity, immunosenescence and cardiovascular aging in humans, 2019, bioRxiv pp. 1-66.
Zhou et al., Resveratrol regulates mitochondrial reactive oxygen species homeostasis through SIRT3signaling pathway in human vascular . . . , 2014, Cell Death Dis vol. 5, pp. 1-8.
U.S. Appl. No. 16/878,308, filed May 19, 2020. A Precision Medicine Method for Cancer Immunotherapy.
U.S. Appl. No. 16/970,796, filed Aug. 18, 2020. Methods for Measuring Systemic Chronic Inflammation.
U.S. Appl. No. 17/226,778, filed Apr. 9, 2021. Compounds and Methods for Modifying iAge.
U.S. Appl. No. 17/329,978, filed May 25, 2021. Treatment and Prevention of Cardiovascular Disease.

\* cited by examiner

TREATMENT AND PREVENTION OF CARDIOVASCULAR DISEASE

BACKGROUND

Cardiovascular disease, such as ischaemic heart disease (IHD) and stroke constitutes the main causes of death in most economically developed countries, accounting for about a third of all adult deaths. There were 200,000 deaths from cardiovascular disease in England and Wales in 1998 in men and women over the age of 15, including death from heart disease and stroke and the smaller numbers of deaths from other cardiovascular causes that relate to the major cardiovascular risk factors.

The main environmental causes of these diseases, apart from cigarette smoking, are dietary and other lifestyle factors that increase the established risk factors of blood pressure, plasma or serum cholesterol (hereinafter simply referred to as serum cholesterol), plasma or serum homocysteine (hereinafter simply referred to as serum homocysteine), and impaire platelet function and coagulation. Realistic changes to lifestyle factors (dietary change, weight loss, increased exercise etc.) do not generally produce sufficient change in the cardiovascular risk factors to substantially reduce cardiovascular risk, so drug treatment to reduce the risk factors is commonly used.

The present policy for such drug treatment for reducing the incidence of cardiovascular diseases in the general population is based on intervention only when the level of one of these risk factors (especially blood pressure) is found to be particularly high (approximately the top 5% of the distribution in middle aged people and the top 10% in elderly people). Drugs have tended to be used specifically for the control of high values of each risk factor: an individual found to have what is regarded as high blood pressure but an average serum cholesterol concentration will be given treatment to lower the blood pressure but no treatment to lower the serum cholesterol. Drugs to alter platelet function (such as, for example, aspirin) and to lower serum homocysteine (such as, for example, folic acid) are rarely recommended for healthy persons. In persons who have had a non-fatal heart attack or stroke, treatment aimed at lowering blood pressure is given only if the blood pressure is at a level regarded as high (about top 10%), cholesterol lowering treatment is given if serum cholesterol is in roughly the upper half of the cholesterol distribution in the population, aspirin is routinely given, folic acid is generally not given.

Described herein is a new paradigm for assessing and treating cardiovascular disease based on the intracellular or extracellular levels of chronic inflammation (iAge, cytokine response score CRS, and/or Jak-STAT response) of a subject followed by the design of individualized therapies aimed to improve outcomes in cardiovascular disease.

SUMMARY

The disclosure describes a method for treating cardiovascular disease patients or patients at risk of cardiovascular disease whereby subjects can be stratified based on risk for cardiovascular disease based on their inflammatory factor level; and can receive individualized interventions to treat and/or reduce the inflammatory factors and improve their risk profile, cardiovascular health, and response to cardiovascular treatments.

An inflammatory age scoring system (iAge) can be used to classify patients into those who have higher risk for cardiovascular disease versus those who have a low risk. The inflammatory age scoring system can be used to guide initial therapy targeting inflammation to improve outcomes of patients receiving treatment for cardiovascular disease, and to reduce risk of cardiovascular disease in asymptomatic patients (e.g., prophylactic treatment). MIG, EOTAXIN, Mip-1α, LEPTIN, IL-1β, IL-5, IFN-α and IL-4 (positive contributors) and TRAIL, IFN-γ, CXCL1, IL-2, TGF-α, PAI-1 and LIF (negative contributors) are related to iAge and can be used to make up the iAge score. MIG, LIF and Sirtuin-3 are strongly related to cardiac aging and risk for cardiovascular disease and can be used alone or combination with other factors to define the risk level of a patient.

Based on a subject's iAge, CRS, Jak-STAT responses, cAge, and/or levels of MIG, LIF and/or SIRT3 the subject can be classified as high risk or low risk for cardiovascular disease. Patients who are classified as high risk can be treated to lower their iAge, increase their CRS, increase their Jak-STAT response, lower cAge, lower MIG, raise LIF and/or raise SIRT3 so that the subject moves into the low risk category. Classifications are made by comparing the subject's iAge, CRS, Jak-STAT responses, cAge, and/or levels of MIG, LIF and/or SIRT3 to those of patients of similar chronological age. When a subject's iAge, CRS, Jak-STAT responses, cAge, and/or levels of MIG, LIF and/or SIRT3 places them at a younger iAge for their age cohort, or a more responsive CRS and/or Jak-STAT score, a lower cAge, a lower MIG, a higher LIF, and/or a higher SIRT3 the subject is less at risk for cardiovascular disease. Subjects with older iAge for their age cohort, lower scores for CRS and/or Jak-STAT, older cAge, a higher MIG, a lower LIF, and/or a lower SIRT3 can be treated to lower their iAge, increase their CRS and/or Jak-STAT score, lower cAge, lower MIG, increase LIF, and/or increase SIRT3 so that they move into the lower risk cohort of patients.

A subject's MIG, LIF, and Sirtuin-3 levels can also be used to classify risk for cardiovascular disease. Patients can be classified by their levels of MIG, Sirtuin-3, LIF, and optionally other factors. For example, the patients can be assigned a cardiac age based on these factors with or without other factors. When a patient's levels of MIG, SIRT3, LIF, and/or cardiac age (cAge) places them in a younger quartile, quintile, decile (or other quantile) for their age cohort the subject is less at risk for cardiovascular disease. Subjects with older levels of MIG, SIRT3, LIF, and/or cAge for their age cohort can be treated to lower their levels of MIG, SIRT3, LIF, and/or cAge so that they move into the lower risk cohort of patients.

In an aspect, the disclosure describes diagnosing cardiovascular disease, monitoring cardiovascular disease progression, monitoring the treatment of cardiovascular disease, prognosing cardiovascular disease, treating cardiovascular disease, alleviating symptoms of cardiovascular disease, inhibiting progression of cardiovascular disease, and preventing cardiovascular disease, in a mammal using the markers, combinations of markers, treatments, prophylactic treatments, and/or agents provided herein.

DETAILED DESCRIPTION

Figure 1A:
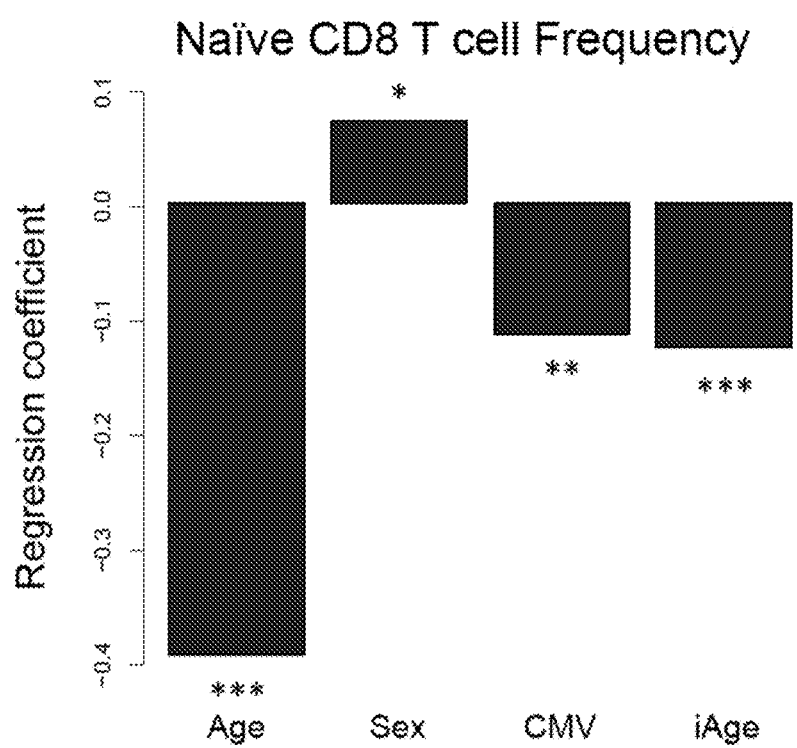
FIGS. 1A, 1B and 1C show graphs of iAge, naïve CD8(+) T-cells, and Jak STAT signaling responses.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 µg, it is intended that the concentration be understood to be at least approximately or about 10 µg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, "activation" is defined to be a physiological condition upon exposure to a substance, allergen, drug, protein, chemical, or other stimulus, or upon removal of a substance, allergen, drug, protein, chemical or other stimulus.

As used herein, an "antibody" is defined to be a protein functionally defined as a ligand-binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies exist as intact immunoglobulins, as a number of well characterized fragments produced by digestion with various peptidases, or as a variety of fragments made by recombinant DNA technology. Antibodies can derive from many different species (e.g., rabbit, sheep, camel, human, or rodent, such as mouse or rat), or can be synthetic. Antibodies can be chimeric, humanized, or humaneered. Antibodies can be monoclonal or polyclonal, multiple or single chained, fragments or intact immunoglobulins.

As used herein, an "antibody fragment" is defined to be at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either $V_L$ or $V_H$), camelid VHH domains, and multi-specific antibodies formed from antibody fragments. The term "scFv" is defined to be a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

As used herein, an "antigen" is defined to be a molecule that provokes an immune response. This immune response may involve either antibody production, or the activation of specific immunologically-competent cells, or both. The skilled artisan will understand that any macromolecule, including, but not limited to, virtually all proteins or peptides, including glycosylated polypeptides, phosphorylated polypeptides, and other post-translation modified polypeptides including polypeptides modified with lipids, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be synthesized or can be derived from a biological sample, or can be a macromolecule besides a polypeptide. Such a biological sample can include, but is not limited to a tissue sample, a tumor sample, a cell or a fluid with other biological components.

As used herein, an "effective amount" or "therapeutically effective amount" are used interchangeably, and defined to be an amount of a compound, formulation, material, or composition, as described herein effective to achieve a particular biological result.

As used herein, an "epitope" is defined to be the portion of an antigen capable of eliciting an immune response, or the portion of an antigen that binds to an antibody. Epitopes can be a protein sequence or subsequence that is recognized by an antibody.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will be an expression vector or expression construct.

As used herein, "heart failure" often called congestive heart failure (CHF) or congestive cardiac failure (CCF), means a condition that occurs when the heart is unable to provide sufficient pump action to maintain blood flow to meet the needs of the body. Heart failure can cause a number of symptoms including shortness of breath, leg swelling, and exercise intolerance. The condition is typically diagnosed by patient physical examination and confirmed with echocardiography. Common causes of heart failure include myocardial infarction and other forms of ischemic heart disease, hypertension, valvular heart disease, and cardiomyopathy. The term heart failure is sometimes incorrectly used for other cardiac-related illnesses, such as myocardial infarction (heart attack) or cardiac arrest, which can cause heart failure but are not equivalent to heart failure.

As used herein, "heterologous" is defined to mean the nucleic acid and/or polypeptide is not homologous to the host cell. Alternatively, "heterologous" means that portions of a nucleic acid or polypeptide that are joined together to make a combination where the portions are from different species, and the combination is not found in nature.

As used herein, the term "impaired immune function" is defined to be any reduction in immune function in an individual, as compared to a fully healthy individual. Individuals with an impaired immune function are readily identifiable by substantially increased abundance of CD8+ CD28− cells or more broadly by reduced cytokine responses, increased baseline phosphoprotein levels and other co-occurring measure.

As used herein, the term "inflammasome" is defined as cytosolic multiprotein complexes that are composed of an inflammasome-initiating sensor, apoptosis-associated speck-like protein containing a CARD (Caspase Activation and Recruitment Domain) acts as an adaptor protein and the protease-caspase-1. Inflammasome-initiating sensors include members of the NLRs the pyrin and HIN domain-containing (also known as PYHIN, Aim 2-like receptors, or ALRs; e.g., Aim2), or the TRIM (e.g., pyrin) family. Complex assembly leads to caspase-1-dependent cleavage of cytokines pro-interleukin 1β (pro-IL-1β) and pro-IL-18 into secreted mature forms. In addition, inflammasomes initiate pyroptotic cell death.

As used herein, a "single chain antibody" (scFv) is defined as an immunoglobulin molecule with function in antigen-binding activities. An antibody in scFv (single chain fragment variable) format consists of variable regions of heavy ($V_H$) and light ($V_L$) chains, which are joined together by a flexible peptide linker.

Immunological Age and Cardiac Age

The Jak/STAT signaling pathway is critical for meeting the multiple challenges encountered by the immune system, from fighting infections to maintaining immune tolerance. Clearly STATs are also involved in the development and function of the immune system in humans and play a key role in maintaining immune surveillance of cancer (Nature. 2007; 450(7171):903-7; Nat Rev Cancer (2009) 9:798-809).

The Jak-STAT pathway can be profoundly altered with aging and this is one major cause of immune dysfunction in older adults. A cytokine response score (CRS) can be used to predict immune decline and reduction in immune surveillance of cancer.

An inflammatory age scoring system (iAge) can also be used to predict age-associated multimorbidity and mortality. iAge can be extremely sensitive as a biomarker of cardiovascular health since elevated levels predict left ventricular remodeling and arterial stiffness even in very healthy older subject with no clinical or laboratory cardiovascular risk factors. iAge can also identify subclinical immunodeficient young patients (10% of subjects 16-35 years old) who cannot mount responses to any strain of the influenza vaccine in any of the years studied (up to 6 years follow-up). These subjects are characterized by having an older-like immunological phenotype with regards to their immune cell composition, ex vivo responses to multiple acute stimuli, and expression of gene modules associated with advanced age.

Since the cytokine response score CRS and iAge are independent measures of inflammation, diminished Jak-STAT signaling pathway in T cells, and low naïve CD8(+) T cell counts (FIG. 1A-C) these measures can be used to stratify cancer patients with respect to their clinical responses to immunotherapy. The methods described herein use blood inflammatory markers CRS and iAge to stratify cancer patients into responder and nonresponders groups for immunotherapy. The nonresponders can be treated to reduce their iAge and/or increase their CRS (and/or Jak-STAT score) so that the nonresponders obtain iAge and/or CRS (and/or Jak-STAT score) that places them into a responder group.

Figure 2:
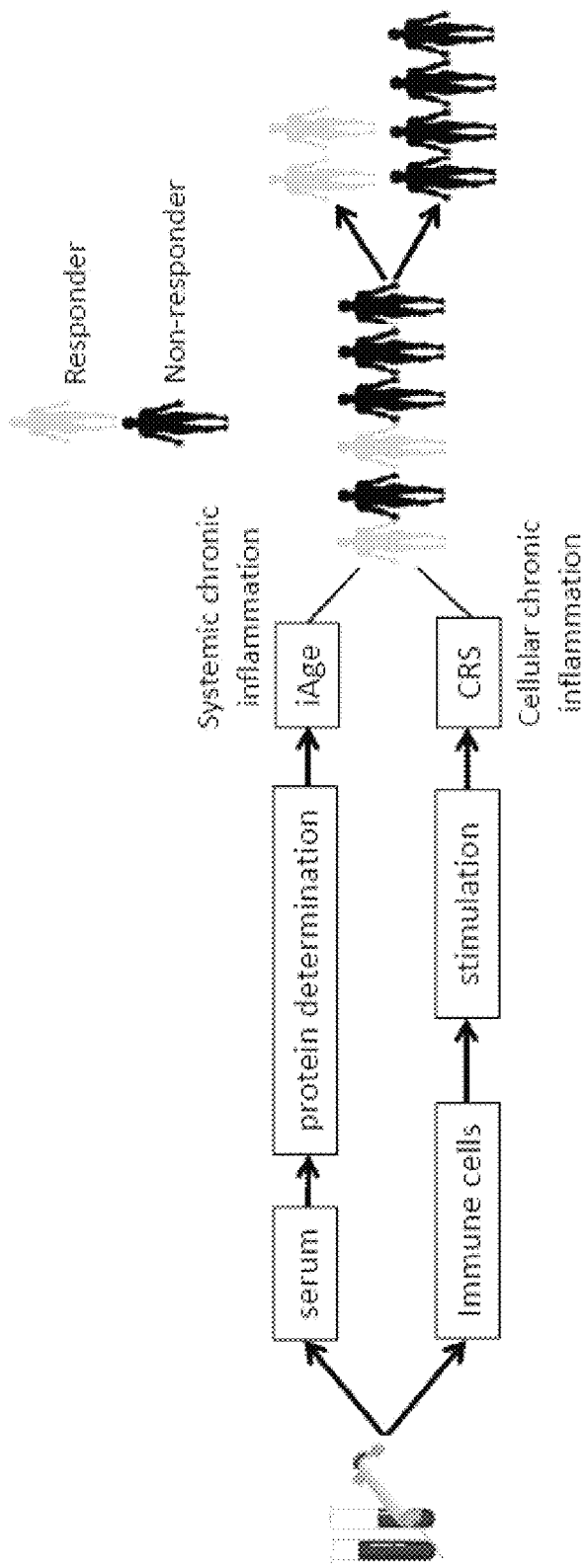
FIG. 2 shows the stratification of cancer patients by iAge and CRS into responders and nonresponders.

The procedure involves the extraction of peripheral blood samples by venipuncture, or by any appropriate method, from candidate cancer patients prior to infusion with immunotherapy treatment (FIG. 2). Immunotherapy treatment may comprise the use of certain molecules including antibodies, small molecules, etc. against inhibitory immune receptors. Blood serum is separated from blood cells by centrifugation of clogged blood, or by any other appropriate method (FIG. 2).

Construction of iAge: For serum protein determination, the resulting sera can be mixed with antibody-linked magnetic beads on 96-well filter-bottom plates and can be incubated at room temperature for 2 h followed by overnight incubation at 4° C. Room temperature incubation steps can be performed at an orbital shaker at 500-600 rpm. Plates can be vacuum filtered and washed twice with wash buffer, then incubated with biotinylated detection antibody for 2 h at room temperature. Samples can be then filtered and washed twice as above and re-suspended in streptavidin-PE. After incubation for 40 minutes at room temperature, two additional vacuum washes can be performed, and the samples can be re-suspended in Reading Buffer. Each sample can be measured in duplicate or triplicate. Plates can be read using a Luminex 200 instrument with a lower bound of 100 beads per sample per cytokine and mean fluorescence intensity (MFI) is recorded.

To derive inflammatory age (iAge) (FIG. 2), the mean fluorescence intensity can be normalized and used for multiple regression analysis, which is computed using the following regression coefficients: MIG: 0.6357, TRAIL: −0.3760, IFNG: −0.3235, EOTAXIN: 0.2912, GROA: −0.2723, IL2: −0.2063, TGFA: −0.1978, PAI1: −0.1587, LIF: −0.1587, LEPTIN: 0.1549, MIP1A: 0.1547, IL1B: 0.1471. The MFI can be multiplied by the regression coefficient for the protein, and these numbers can be all added together to give the iAge of the subject. Table 1 below lists the ranges of iAge within chronological age decades.

TABLE 1 iAge Ranges

| Chronological Age (years) | iAge Range |
|---|---|
| 10-19 | 18.1-58.3 |
| 20-29 | 18.5-78.9 |
| 30-39 | 16.9-70.2 |
| 40-49 | 21.5-74.1 |
| 50-59 | 23.1-74.4 |
| 60-69 | 28.1-76.6 |
| 70-79 | 35.6-77.6 |
| 80-96 | 37.9-78.5 |

Those markers with positive regression coefficients increased in serum concentration with age (MIG, EOTAXIN, LEPTIN, MIP1A, and IL1B) and those with negative regression coefficients decreased in serum concentration with age (TRAIL, IFNG, GROA, IL2, TGFA, PAI1, and LIF).

MIG (monokine induced by gamma interferon) is a small cytokine belonging to the CXC chemokine family. MIG is one of the chemokines which plays a role to induce chemotaxis, promote differentiation and multiplication of leukocytes, and cause tissue extravasation. MIG regulates immune cell migration, differentiation, and activation. Tumor-infiltrating lymphocytes are a key for clinical outcomes and prediction of the response to checkpoint inhibitors. In vivo studies suggest the axis plays a tumorigenic role by increasing tumor proliferation and metastasis. MIG predominantly mediates lymphocytic infiltration to the focal sites and suppresses tumor growth. MIG binds to C-X-C motif chemokine 3 of the CXCR3 receptor.

TRAIL (TNF-related apoptosis-inducing ligand) is a cytokine that is produced and secreted by most normal tissue cells. It is thought to cause apoptosis primarily in tumor cells by binding to certain death receptors. TRAIL has also been designated CD253 (cluster of differentiation 253) and TNFSF1O (tumor necrosis factor (ligand) superfamily, member 10). TRAIL is described in Wiley et al Immunity 1005 3: 673-82 as well as Pitti J. Biol. Chem. 1996 271: 12687-90.

INFG (otherwise known as interferon gamma, IFNγ or type II interferon) is a dimerized soluble cytokine that is the only member of the type II class of interferons. IFNG is critical for innate and adaptive immunity against viral, some bacterial and protozoan infections. INFG is an important activator of macrophages and inducer of Class II major histocompatibility complex (MHC) molecule expression. INFG is described In Schoenborn et al Adv. Immunol. 2007 96: 4I-IOI as well as Gray Nature. I982 298: 859-63.

Eotaxin (also known as C-C motif chemokine I I or eosinophil chemotactic protein) is a small cytokine belonging to the CC chemokine family. Eotaxin selectively recruits eosinophils by inducing their chemotaxis, and therefore, is implicated in allergic responses. The effects of eotaxin is mediated by its binding to a G-protein-linked receptor known as a chemokine receptor. Chemokine receptors for which CCLII is a ligand include CCR2, CCR3 and CCR5. Eotaxin is described in Kitaura et al The Journal of Biological Chemistry I 996 27I: 7725-30 and Jose et al The Journal of Experimental Medicine I994 I 79: 88I-7.

GROA (also known as CXCLI, the GROI oncogene, GROa, KC, neutrophilactivating protein 3 (NAP-3) and melanoma growth stimulating activity, alpha (MSGA-a)) is secreted by human melanoma cells, has mitogenic properties and is implicated in melanoma pathogenesis. GROA is expressed by macrophages, neutrophils and epithelial cells, and has neutrophil chemoattractant activity. This chemokine elicits its effects by signaling through the chemokine receptor CXCR2. GROA is described in Haskill et al Proc. Natl. Acad. Sci. U.S.A. I90 87 (I9): 7732-6.

IL-2 is one of the key cytokines with pleiotropic effects on the immune system. It is a 15.5-16 kDa protein that regulates the activities of white blood cells (leukocytes, often lymphocytes) that are responsible for immunity. The major sources of IL-2 are activated CD4+ T cells, activated CD8+ T cells, NK cells, dendritic cells and macrophages. IL-2 is an important factor for the maintenance of CD4+ regulatory T cells and plays a critical role in the differentiation of CD4+ T cells into a variety of subsets. It can promote CD8+ T-cell and NK cell cytotoxicity activity, and modulate T-cell differentiation programs in response to antigen, promoting naive CD4+ T-cell differentiation into T helper-1 (Th1) and T helper-2 (Th2) cells while inhibiting T helper-17 (Th17) differentiation.

TGFA (transforming growth factor alpha) is a polypeptide of 5.7 kDa that is partially homologous to EGF. TGFA is a growth factor that is a ligand for the epidermal growth factor receptor, which activates a signaling pathway for cell proliferation, differentiation and development. TGFA also is a potent stimulator of cell migration. TGFA can be produced in macrophages, brain cells, and keratinocytes. TGFA can induce epithelial development. TGFA can also upregulate TLR expression and function augmenting host cell defense mechanisms at epithelial surfaces. TGFA may act as either a transmembrane-bound ligand or a soluble ligand. TGFA has been associated with many types of cancers, and it may also be involved in some cases of cleft lip/palate. Alternatively spliced transcript variants encoding different isoforms have been found for this gene.

PAI1 (plasminogen activator inhibitor-1) is a member of the serine proteinase inhibitor (serpin) superfamily. PAI1 is the principal inhibitor of tissue plasminogen activator (tPA) and urokinase (uPA), and hence is an inhibitor of fibrinolysis. PAI1 is also a regulator of cell migration. PAI1 can play a role in a number of age-related, conditions including, for example, inflammation, atherosclerosis, insulin resistance, obesity, comorbidities, and Werner syndrome. PAI1 can play a host protective role during the acute phase of infection by regulating interferon gamma release. IFNG regulates PAI-1 expression, which suggests an intricate interplay between PAI-1 and IFNG. PAI1 can also activate macrophages through Toll-like receptor 4 (TLR4) and can promote migration of pro-cancer M2 macrophages into tumors.

LIF (leukemia inhibitory factor) is interleukin 6 class cytokine with pleiotropic effects impacting several different systems. When LIF levels drop, cells differentiate. LIF has the capacity to induce terminal differentiation in leukemic cells. Its activities include the induction of hematopoietic differentiation in normal and myeloid leukemia cells, the induction of neuronal cell differentiation, and the stimulation of acute-phase protein synthesis in hepatocytes. The protein encoded by this gene is a pleiotropic cytokine with roles in several different systems. It is involved in the induction of hematopoietic differentiation in normal and myeloid leukemia cells, induction of neuronal cell differentiation, regulator of mesenchymal to epithelial conversion during kidney development, and may also have a role in immune tolerance at the maternal-fetal interface. Alternatively spliced transcript variants encoding multiple isoforms have been observed for this gene. LIF functions through both autocrine and paracrine manners. LIF binds to its specific receptor LIFR, then recruits gp130 to form a high affinity receptor complex to induce the activation of the downstream signal pathways including JAK/STAT3, PI3K/AKT, ERK1/2 and mTOR signaling. Further studies have clearly proven that LIF is a multifunctional protein which has a broad biological functions in neuronal, hepatic, endocrine, inflammatory and immune systems. LIF regulates the embryonic stem cell self-renewal and is an indispensable factor to maintain mouse embryonic stem cell pluripotency. The expression of LIF is induced under inflammatory stress as an anti-inflammatory agent.

LEPTIN is secreted by white adipocytes into the circulation and plays a major role in the regulation of energy homeostasis. LEPTIN binds to the leptin receptor in the brain, which activates downstream signaling pathways that inhibit feeding and promote energy expenditure. LEPTIN also has several endocrine functions, and is involved in the regulation of immune and inflammatory responses, hematopoiesis, angiogenesis, reproduction, bone formation and wound healing. LEPTIN can directly link nutritional status and pro-inflammatory T helper 1 immune responses, and a decrease of LEPTIN plasma concentration during food deprivation can lead to an impaired immune function. LEPTIN is associated with the pathogenesis of chronic inflammation, and elevated circulating LEPTIN levels in obesity appear to contribute to low-grade inflammation which makes obese individuals more susceptible to increased risk of developing cardiovascular diseases, type II diabetes, and degenerative disease including autoimmunity and cancer. Reduced levels of LEPTIN such as those found in malnourished individuals have been linked to increased risk of infection and reduced cell-mediated immune responses. Mutations in this gene and its regulatory regions cause severe obesity and morbid obesity with hypogonadism in human patients. A mutation in this gene has also been linked to type 2 diabetes mellitus development.

MIP1A (macrophage inflammatory protein) is a member of the CC or beta chemokine subfamily. MIP1A regulates leukocyte activation and trafficking. MIP1A acts as a chemoattractant to a variety of cells including monocytes, T cells, B cells and eosinophils. MIP1A plays a role in inflammatory responses through binding to the receptors CCR1, CCR4 and CCR5.

IL-1B (Interleukin-1 beta) is a member of the interleukin 1 cytokine family. IL-1B is an important mediator of the inflammatory response, and is involved in a variety of cellular activities, including cell proliferation, differentiation, and apoptosis. LI-1B is produced by activated macrophages as a proprotein, which is proteolytically processed to its active form by caspase 1 (CASP1/ICE).

iAge predicts pulse-wave velocity (a measure of arterial stiffness, or the rate at which pressure waves move down the vessel) which correlates with cardiovascular health.

Construction of CRS: Separation of immune cells may comprise the use of differential centrifugation of blood by density gradient (FIG. 2). The resulting cell pellet can be suspended in warm media, wash twice and resuspended at 0.5×10^6 viable cells/mL. 200 uL of cell sample can be plated per well in 96-well deep-well plates. After resting for 1 hour at 37° C., cells can be stimulated by adding 50 ul of cytokine (IFNa, IFNg, IL-6, IL-7, IL-10, IL-2, or IL-21) (FIG. 2) and incubated at 37° C. for 15 minutes. The cells can be fixed with paraformaldehyde, permeabilized with methanol, and kept at −80 C overnight. Each well can then be bar-coded using a combination of Pacific Orange and Alexa-750 dyes (Invitrogen, Carlsbad, Calif.) and pooled in tubes. The cells can be washed with FACS buffer (PBS supplemented with 2% FBS and 0.1% soium azide), and stained with the following antibodies (all from BD Biosciences, San Jose, Calif.): CD3 Pacific Blue, CD4 PerCP-Cy5.5, CD20 PerCp-Cy5.5, CD33 PE-Cy7, CD45RA Qdot 605, pSTAT-1 AlexaFluor488, pSTAT-3 AlexaFluor647, pSTAT-5 PE. The samples can be washed and resuspended in FACS buffer. 100,000 cells per stimulation condition are collected using DIVA 6.0 software on an LSRII flow cytometer (BD Biosciences). Data analysis can be performed using FlowJo v9.3 by gating on live cells based on forward versus side scatter profiles, then on singlets using forward scatter area versus height, followed by cell subset-specific gating.

Fold-change difference due to stimulation can be computed as the ratio of the cell, cytokine stimulation, phosphoprotein measure to the raw, un-normalized, cell-phosphoprotein matching baseline that was measured on the same plate. The data can be normalized by scaling individual's by the average of the assay on the day in which they were measured.

To construct the Cytokine Response Score (CRS) (FIG. 2) 15 reproducible age-associated normalized cytokine responses can be expressed as fold increases over baseline (unstimulated) and the fold increases for the following can be summed: CD8+ cells, stimulate with IFNa and measure pSTAT1, 3 and 5; CD8+ cells, stimulate with IL6 and measure pSTAT1, 3 and 5, CD8+ cells, stimulate with IFNg and measure pSTAT1, CD8+ cells, stimulate with IL21 and measure pSTAT1; CD4+ cells, stimulate with IFNa and measure pSTAT5, CD4+ cells, stimulate with IL6 and measure pSTAT5, CD20+ cells, stimulate with IFNa and measure pSTAT1, Monocytes stimulate with IL10 and measure pSTAT3, Monocytes stimulate with IFNg and measure pSTAT3, Monocytes stimulate with IFNa and measure pSTAT3, and Monocytes stimulate with IL6 and measure pSTAT3.

IFNA (Interferon alpha) is a member of the type I interferon class. And has thirteen (13) variants in humans. IFNA is secreted by hematopoietic cells, predominately plasmacytoid dendritic cells. IFNA can have either protective or deleterious roles. IFNA can be induced by ssRNA, dsRNA, and cytosolic DNA from viruses or bacteria. IFNA can induce caspase-11 expression, which contributes to activation of non-canonical inflammasome. Use of recombinant IFNA has been shown to be effective in reducing the symptoms and duration of the common cold.

INFG (Interferon gamma) is a member of the type II interferon class. The encoded protein is secreted by cells of both the innate and adaptive immune systems. The active protein is a homodimer that binds to the interferon gamma receptor which triggers a cellular response to viral and microbial infections. Mutations in this gene are associated with an increased susceptibility to viral, bacterial and parasitic infections and to several autoimmune diseases.

IL6 is a cytokine with pleiotropic effects on inflammation, immune response, and hematopoiesis. IL6 is promptly and transiently produced in response to infections and tissue injuries, contributes to host defense through the stimulation of acute phase responses, hematopoiesis, and immune reactions. IL6 functions in inflammation and the maturation of B cells. In addition, IL6 has been shown to be an endogenous pyrogen capable of inducing fever in people with autoimmune diseases or infections. IL6 is primarily produced at sites of acute and chronic inflammation, where it is secreted into the serum and induces a transcriptional inflammatory response through interleukin 6 receptor, alpha. IL6 is implicated in a wide variety of inflammation-associated disease states, including susceptibility to diabetes mellitus and systemic juvenile rheumatoid arthritis. Dysregulated, continual synthesis of IL-6 plays a pathological effect on chronic inflammation and autoimmunity. Alternative splicing results in multiple transcript variants.

IL10 is a cytokine with pleiotropic effects in immunoregulation and inflammation. IL-10 is an anti-inflammatory cytokine and during infection it inhibits the activity of Th1 cells, NK cells, and macrophages, all of which are required for optimal pathogen clearance but also contribute to tissue damage. IL10 can directly regulate innate and adaptive Th1 and Th2 responses by limiting T cell activation and differentiation in the lymph nodes as well as suppressing proinflammatory responses in tissues. It also enhances B cell survival, proliferation, and antibody production. This cytokine can block NF-kappa B activity, and is involved in the regulation of the JAK-STAT signaling pathway. Knockout studies in mice suggested the function of this cytokine as an essential immunoregulator in the intestinal tract.

IL21 is a member of the common-gamma chain family of cytokines with immunoregulatory activity. IL21 plays a role in both the innate and adaptive immune responses by inducing the differentiation, proliferation and activity of multiple target cells including macrophages, natural killer cells, B cells, cytotoxic T cells, and epithelial cells. IL21 is important to anti-tumor and antiviral responses and also exerts major effects on inflammatory responses that promote the development of autoimmune diseases and inflammatory disorders.

pSTAT1 (phosphorylated signal transducer and activator of transcription 1) mediates cellular responses to interferons (IFNs), cytokine KITLG/SCF and other cytokines and other growth factors. Following type I IFN (IFN-alpha and IFN-beta) binding to cell surface receptors, signaling via protein kinases leads to activation of Jak kinases (TYK2 and JAK1) and to tyrosine phosphorylation of STAT1 and STAT2. The phosphorylated STATs dimerize and associate with ISGF3G/IRF-9 to form a complex termed ISGF3 transcription factor, that enters the nucleus (PubMed:28753426). ISGF3 binds to the IFN stimulated response element (ISRE) to activate the transcription of IFN-stimulated genes (ISG), which drive the cell in an antiviral state. In response to type II IFN (IFN-gamma), STAT1 is tyrosine- and serine-phosphorylated (PubMed:26479788). It then forms a homodimer termed IFN-gamma-activated factor (GAF), migrates into the nucleus and binds to the IFN gamma activated sequence (GAS) to drive the expression of the target genes, inducing a cellular antiviral state.

pSTAT 3 (phosphorylated signal transducer and activator of transcription 3) mediates cellular responses to interleukins, KITLG/SCF, LEP and other growth factors. Once activated, recruits coactivators, such as NCOA1 or MED1, to the promoter region of the target gene. Binds to the interleukin-6 (IL-6)-responsive elements identified in the promoters of various acute-phase protein genes. Activated by IL31 through IL31RA. Acts as a regulator of inflammatory response by regulating differentiation of naive CD4+ T-cells into T-helper Th17 or regulatory T-cells (Treg): deacetylation and oxidation of lysine residues by LOXL3, disrupts STAT3 dimerization and inhibits its transcription activity.

pSTAT 5 (phosphorylated signal transducer and activator of transcription 5) is activated by Janus-activated kinases (JAK) downstream of cytokine receptors. STAT5 proteins are activated by a wide variety of hematopoietic and non-hematopoietic cytokines and growth factors, all of which use the JAK-STAT signaling pathway as their main mode of signal transduction. STAT5 proteins critically regulate vital cellular functions such as proliferation, differentiation, and survival. STAT5 plays an important role in the maintenance of normal immune function and homeostasis, both of which are regulated by specific members of IL-2 family of cytokines, which share a common gamma chain ($\gamma(c)$) in their receptor complex. STAT5 critically mediates the biological actions of members of the $\gamma(c)$ family of cytokines in the immune system. Essentially, STAT5 plays a critical role in the function and development of Tregs, and consistently activated STAT5 is associated with a suppression in antitumor immunity and an increase in proliferation, invasion, and survival of tumor cells.

Construction of Cardiac Age.

To derive Cardiac age (cAge), patient samples are obtained and processed similar to the description above for iAge. The mean fluorescence intensity can be normalized and used for multiple regression analysis. The levels of MIG, LIF and SIRT3 are diagnostic for risk of cardiovascular health. Other parameters that can be used to compute cardiac age include, for example, aortic pulse wave velocity, a measure of vascular stiffness; relative wall thickness (RWT), a measure of ventricular remodeling, and early diastolic mitral annular velocities (e'), a measure of ventricular relaxation. Still other parameters include, for example, sex, BMI, heart rate, systolic blood pressure, fasting glucose and total cholesterol to HDL ratio. The levels of MIG, LIF, SIRT3, and/or other measurements for a subject can be compared to those of other subjects of the same age and/or different ages to determine the quantile of the subject for each factor, or for the factors of subjects of different ages. Low quantile rank for MIG is diagnostic for low risk of cardiovascular disease, and high quantile rank for MIG is diagnostic for a higher risk of cardiovascular disease. High quantile rank for LIF and/or SIRT3 are diagnostic for low risk of cardiovascular disease, and high quantile rank for LIF and/or SIRT3 are diagnostic for a higher risk of cardiovascular disease. Other parameters (factors) can also be included in the analysis and, for example, high quantile rank for pulse wave velocity are diagnostic for a higher risk of cardiovascular disease, high quantile rank for abnormal RWT are diagnostic for a higher risk of cardiovascular disease, and lower quantile early diastolic mitral annular velocities are also diagnostic for higher risk of cardiovascular disease. Multiple parameters and/or factors can be combined to compute cardiac age, for example, MIG, LIF and SIRT3 can be used to derive cardiac age, or these factors can be combined with other parameters (e.g., aortic pulse wave velocity, RWT, and/or early diastolic mitral annular velocities) to derive cardiac age. When these factors and/or parameters are combined, high quantile rank will correlate with older cardiac age and a higher risk of cardiovascular disease, and a low quantile rank will correlate with younger cardiac age and a lower risk of cardiovascular disease. Quantile ranks can include, for example, quartiles, quintiles or deciles.

SIRT3 (Situin-3, a NAD-dependent deacetylase) is member of the mammalian sirtuin family of proteins, which are homologs to the yeast Sir2 protein. SIRT3 exhibits NAD+-dependent deacetylase activity. SIRT3 is a regulator of the mitochondrial adaptive response to stress, such as metabolic reprogramming and antioxidant defense mechanisms. SIRT3 mediates cellular resistance toward various forms of stress by maintaining genomic stability and mitochondrial integrity. SIRT3 is central to the maintenance of appropriate mitochondrial function by limiting oxidative stress, and reducing reactive oxygen species (ROS) production with a decrease in mitochondrial membrane potential. SIRT3 has cardio-protective properties involved in mitochondrial homeostasis, stem cell and tissue maintenance during aging, and linked to the beneficial effects of diet, caloric restriction and exercise in maintaining cardiovascular health and longevity.

MIG positively correlates with cardiovascular aging markers PWV (R=0.22), a measure of arterial stiffness, and RWT (R=0.3), a measure of cardiac remodeling; and a negative correlation between LIF and PWV (R=−0.27), and RWT (R=−0.22). Subclinical cardiac tissue remodeling and increased arterial stiffness can be found in otherwise healthy individuals with elevated levels of MIG and low levels of LIF.

Patients with subclinical cardiac tissue remodeling and increased arterial stiffness can be otherwise healthy individuals who have elevated levels of MIG and low levels of SIRT-3 and LIF. Cardiac tissue remodeling and increased arterial stiffness are risk factors associated with poorer outcomes in cardiovascular disease. The largest contributor to the inflammatory clock, MIG, was positively correlated with subclinical levels of arterial stiffness and cardiac remodeling even in healthy older adults with no clinical or laboratory evidence of cardiovascular disease. The inflammatory clock (iAge) can also be used as an early molecular marker for cardiovascular malfunctioning.

At least two sources of MIG-mediated inflammation can ensue with aging based on our findings; one that is age-intrinsic and observed in aging endothelia, and one independent of age (likely as a response to cumulative exposure to environmental insults). In contrast, there was no significant correlation between known disease risk factors (BMI, smoking, dyslipidemia) and the levels of MIG gene or protein expression. MIG overproduction can be caused by cellular aging per-se, which triggers metabolic dysfunction with production of damage-associated molecular patterns (DAMPs) such as adenine and N4-acetylcytidine. These DAMPs can then act through the inflammasome machinery, such as NLRC4, to regulate multiple inflammatory signals including IL-1β and MIG.

Endothelium has a critical role in the etiology of hypertension and arterial stiffness, and more advanced signs of cardiovascular aging such as tissue remodeling and cardiac hypertrophy are often preceded and may be initiated by malfunctioning of aged endothelia. Endothelial cells show a time-dependent increase in MIG transcript levels, which was concomitant with a drop in SIRT3 expression, and with a decrease in the number of vascular networks formed by the endothelial cells. Young endothelia is a target of MIG from other sources, and MIG can down-regulate SIRT3 expression in the endothelial cells. In addition, endothelia cells made from hiPSC (human, induced pluripotent stem cells) but not cardiomyocytes made from hiPSC, express CXCR3 he receptor for MIG. MIG can act both in a paracrine fashion, wherein increasing levels of this chemokine from immune sources affect endothelial cell function, and in an autocrine fashion on endothelial cells likely producing a positive feedback loop where increasing doses of MIG and expression of its receptor in these cells leads to cumulative deterioration of endothelial function in aging. Exposure of endothelial cells to MIG can also reduce the endothelial cell's capacity for forming tubular networks, and MIG can reduce vasorelaxation in the aorta.

Agents for Lowering iAge

Figure 3:
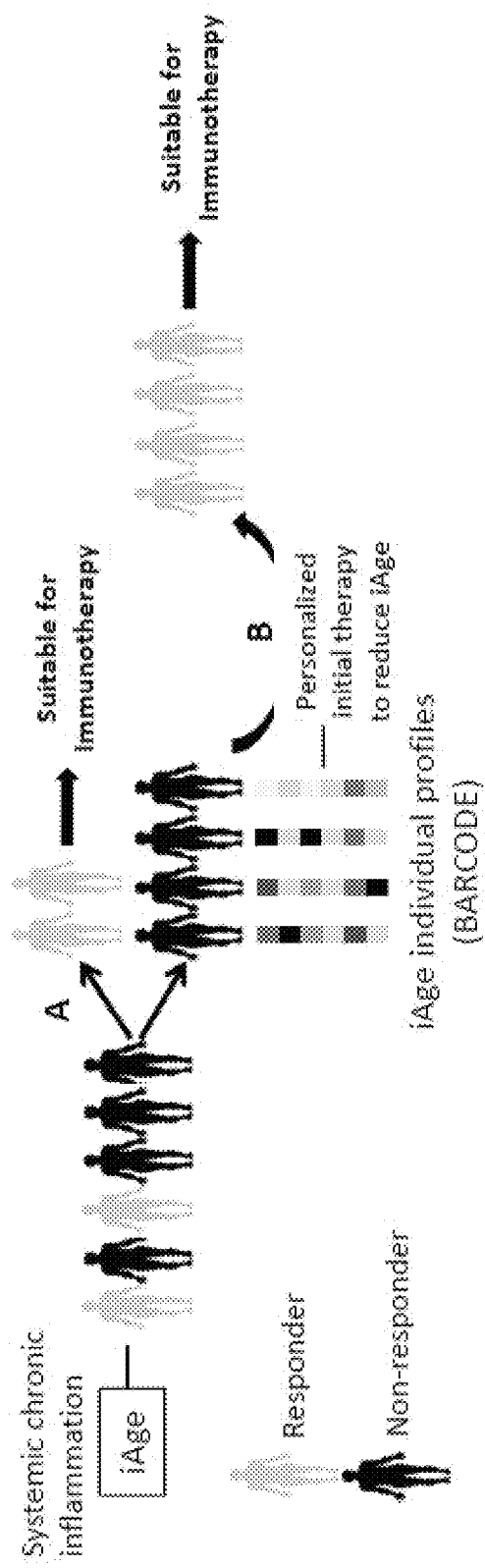
FIG. 3 shows the stratification of cancer patients using iAge.

In addition to using iAge to classify patients (FIG. 3), it can be used to derive individual inflammatory profiles by comparing subject's individual protein levels with those of a population (e.g., of similar chronological age). The resulting signatures (or barcodes) are used for protein-compound association (PCI) analysis using the drugbank database (www.drugbank.ca) and a personalized initial therapy to reduce iAge can be generated (FIG. 3). Patients following personalized recommendations can be monitored weekly for changes in iAge until they reach optimal levels (below group average for a given age bracket) and they convert into a responder to treatment phenotype (FIG. 3). The patient is then classified as a responder and is suitable for immunotherapy treatment.

A subject may reduce their iAge with treatments that lower the levels of TRAIL, IFNG, GROA, IL2, TGFA, PAI1, and/or LIF to their optimal levels for a person's chronological age. A subject may also reduce their iAge with treatments that raise the levels of MIG, EOTAXIN, LEPTIN, IL-1B, or MIP1A to their optimal levels for a person's age.

A subject may also reduce their iAge by reducing any systemic chronic inflammation, using any of the following, whether alone or in combination: (1) pharmacological treatment, including without limitation anti-inflammatory drugs (NSAIDs such as, for example, aspirin, ibuprofen, naproxen, diclofenac, celecoxib, oxaprozin, piroxicam, indomethacin, meloxicam, fenoprofen, diflunisal, etodolac, ketorolac, meclofenamate, nabumetone) or corticosteroids (e.g., glucocorticoids, mineralocorticoids); (2) neutraceuticals or nutritional supplements, including without limitation fish oil, lipoic acid, and curcumin, or spices/herbs such as ginger, garlic, turmeric, hyssop, cannabis, Harpagophytum procumbens, and cayenne; (3) dietary change, including without limitation increasing the intake of foods that are high in antioxidants and polyphenols, such as olive oil, leafy greens (e.g., kale and spinach), broccoli, avocados, green tea, bell peppers, chili peppers, mushrooms, dark chocolate, cocoa, tomatoes, fatty fish (e.g., salmon, sardines, herring, anchovies, and mackerel), nuts (walnuts and almonds), and fruits (e.g., cherries, blackberries, blueberries, raspberries, strawberries, grapes, and oranges), and/or decreasing the intake of foods that can increase inflammation such as refined carbohydrates (e.g., white bread and pastries), high-fructose corn syrup, refined sugar, processed and packaged food, fried foods, red meat, excessive alcohol, and processed meat; and (4) lifestyle changes including without limitation eliminating or reducing smoking and alcohol intake, maintaining a healthy body weight, and reducing stress levels.

Agents for Improving Cardiac Markers

Cardiac markers can be improved by providing a subject with treatments that improve the level of the cardiac marker (lowering cAge). A subject's cardiac marker score (cAge) can be lowered by reducing the MIG in a patient, increasing Sirtuin-3 in the patient, increasing LIF in the patient, and/or reducing cell signaling from CXCR3 (the receptor for MIG). A variety of agents are known which can reduce MIG expression, increase Sirtuin-3 expression, increase LIF activity (or LIF like activity), and/or act as antagonists for CXCR3 (the receptor for MIG).

Agents that can lower MIG (and so improve the cardiac marker and iAge marker) include, for example arsenic trioxide, Roxarsone, Selenium, and/or a variety of antibodies. Antibodies include, for example, MIG-2F5.5 (anti-human CXCL9 antibody, BioLegend Cat. #740072), Anti-human CXCL9 antibody, NSJ Bioreagents, Cat #R30501, Mouse MAb clone 49106 (anti-human CXCL9, R&D Systems Cat #MAB392), Mouse monoclonal MAb for human CXCL9 (neutralizing, GeneTex, Cat #GTX52673), Mouse monoclonal anti-human CXCL9 antibody (OriGene, Cat #PM1209P), MIG Antibody (MM0220-7F11) (Novus Biologicals, NBP2-12236), MIG Antibody (1F5) (Novus Biologicals, H00004283-M06), Mouse MAb anti human CXCL9 (ThermoFisherCat #MA5-23746, Cat #MA5-30320, Cat #MA5-23628, Cat #MA5-23544).

Arsenic trioxide ($As_2O_3$), a component of traditional Chinese medicine, has been used successfully for the treatment of acute promyelocytic leukemia (APL), and $As_2O_3$ is of potential therapeutic value for the treatment of other promyelocytic malignancies and some solid tumors including breast cancer. $As_2O_3$ treatment changed the expression level of several genes that involved in cell cycle regulation, signal transduction, and apoptosis. Notably, $As_2O_3$ treatment increased the mRNA and protein levels of the cell cycle inhibitory proteins, p21 and p27. Interestingly, knocking down p21 or p27 individually did not alter $As_2O_3$-induced apoptosis and cell cycle arrest; however, the simultaneous down-regulation of both p21 and p27 resulted in attenuating of G1, G2/M arrest and reduction in apoptosis, thus indicating that p21 and p27 as the primary molecular targets of $As_2O_3$.

Roxarsone is an organoarsonic acid where the organyl group is 4-hydroxy-3-nitrophenyl. It has a role as a coccidiostat, an antibacterial drug, an agrochemical and an animal growth promotant. It is an organoarsonic acid and a member of 2-nitrophenols. Roxarsone was found to exhibit a higher angiogenic index than $As^{III}$ at lower concentrations. Increased endothelial nitric oxide synthase (eNOS) activity was observed for roxarsone but not for $As^{III}$-induced angiogenesis. However, $As^{III}$ caused more rapid and pronounced phosphorylation of eNOS.

Selenium (Se) is a potential anticarcinogenic nutrient, and the essential role of Se in cell growth is well recognized but certain cancer cells appear to have acquired a survival advantage under conditions of Se-deficiency. Se can exert its effects through increasing the expression of a humoral defense gene (A2M) and tumor suppressor-related genes (IGFBP3, HHIP) while decreasing pro-inflammatory gene (MIG, HSPB2) expression.

Agents that raise Sirtuin-3 levels include, for example, Berberine and Resveratrol. Berberine (molecular formula $C_{20}H_{19}NO_5$ and molecular weight of 353.36) is the main active component of an ancient Chinese herb Coptis chinensis French, which has been used to treat diabetes for thousands of years. Berberine is an Over-the-Counter (OTC) drug, which is used to treat gastrointestinal infections in China. Berberine has been shown to regulate glucose and lipid metabolism in vitro and in vivo. Berberine is also a potent oral hypoglycemic agent with beneficial effects on lipid metabolism.

Resveratrol (3,5,4'-trihydroxy-trans-stilbene) belongs to polyphenols' stilbenoids group, possessing two phenol rings linked to each other by an ethylene bridge. This natural polyphenol has been detected in more than 70 plant species, especially in grapes' skin and seeds, and was found in discrete amounts in red wines and various human foods. It is a phytoalexin that acts against pathogens, including bacteria and fungi. As a natural food ingredient, numerous studies have demonstrated that resveratrol possesses a very high antioxidant potential. Resveratrol also exhibit antitumor activity, and is considered a potential candidate for prevention and treatment of several types of cancer. Indeed, resveratrol anticancer properties have been confirmed by many in vitro and in vivo studies, which shows that resveratrol is able to inhibit all carcinogenesis stages (e.g., initiation, promotion and progression). Even more, other bioactive effects, namely as anti-inflammatory, anticarcinogenic, cardioprotective, vasorelaxant, phytoestrogenic and neuroprotective have also been reported.

Agents that raise LIF levels include Aminodarone, arsenic trioxide, Azathioprine, Estradiol, Chlorambucil, Clomiphene, Coumaphos, Cyclosporine, decitabine, Cisplatin, Vincristine, Formaldehyde, Glucose, Hydrogen Peroxide, letrozole, Lindane, Methotrexate, Quercetin, Oxyquinoline, resorcinol, resveratrol, Silicon Dioxide, Tretinoin, and troglitazone.

The expression of LIF is regulated by many cytokines. In normal human bone marrow stromal cells, IL-1α, IL-1β, TGF-β and tumor necrosis factor-α (TNF-α) can all increase the transcription of LIF mRNA. The induction of LIF by IL-1β and TNF-α was also observed in gingival fibroblasts and several cell types in human airways. In addition, the induction of LIF expression by other cytokines, including IL-6, IL-2 has been observed in different cell types, including airway smooth-muscles and MT-2 cells. The expression of LIF can also be inhibited by some factors, including 1α, 25-dihydroxyvitamin D3 and dexamethasone. The analysis of the LIF promoter revealed that transcription factor STAT5 can bind to the LIF promoter and induce its expression in myeloid cell lines. In addition, the LIF promoter region contains several ETS binding sites. The binding of ETS transcription factors to the LIF promoter is critical for the induction of LIF in response to T cell activators.

Amiodarone is a primarily a class III antiarrhythmic and is one of the most commonly used anti-arrhythmic drugs. While the United States FDA has labeled amiodarone for the treatment of life-threatening ventricular arrhythmias, the drug is commonly used off-label to treat supraventricular tachyarrhythmias such as atrial fibrillation as well as for the prevention of ventricular tachyarrhythmias (VTs) in high-risk patients. Like other antiarrhythmic drugs of this class, amiodarone works primarily by blocking potassium rectifier currents that are responsible for repolarization of the heart during phase 3 of the cardiac action potential. This potassium channel-blocking effect results in increased action potential duration and a prolonged effective refractory period in cardiac myocytes. Unlike other class III agents, amiodarone also interferes with beta-adrenergic receptors, calcium channels, and sodium channels.

Clomiphene is an ovulatory stimulant designated chemically as 2-[p-(2-chloro-1,2-diphenylvinyl)phenoxy]triethylamine citrate (1:1). It has the molecular formula of C26H28C1NO.C6H8O7 and a molecular weight of 598.09. Clomiphene is capable of interacting with estrogen-receptor-containing tissues, including the hypothalamus, pituitary, ovary, endometrium, vagina, and cervix. It may compete with estrogen for estrogen-receptor-binding sites and may delay replenishment of intracellular estrogen receptors. Clomiphene initiates a series of endocrine events culminating in a preovulatory gonadotropin surge and subsequent follicular rupture. The first endocrine event in response to a course of clomiphene therapy is an increase in the release of pituitary gonadotropins.

Coumaphos is an organothiophosphate insecticide, an organic thiophosphate and an organochlorine compound. It has a role as an agrochemical, an acaricide, an antinematodal drug, an avicide and an EC 3.1.1.8 (cholinesterase) inhibitor. Coumaphos is used for control of a wide variety of insects on cattle and parasitic mites (Varroa jacobson) on bees. It is also used in veterinary medicine for the treatment of screw-worms, maggots, and ear ticks on livestock. In humans coumaphos causes muscarinic effects (parasympathetic), nicotinic effects (sympathetic and motor), and CNS effects associated with massive overstimulation of the chlorinergic system.

Lindane also known as gamma-hexachlorocyclohexane (γ-HCH), gammaxene, and Gammallin is an organochlorine chemical and an isomer of hexachlorocyclohexane that has been used both as an agricultural insecticide and as a pharmaceutical treatment for lice and scabies. Lindane is a neurotoxin that interferes with GABA neurotransmitter function by interacting with the $GABA_A$ receptor-chloride channel complex at the picrotoxin binding site. In humans, lindane affects the nervous system, liver, and kidneys, and may well be a carcinogen.

Oxyquinoline is a heterocyclic phenol and Oxyquinoline Sulfate is its salt, both of which are described as cosmetic biocides for use in cosmetic formulations. Oxyquinoline can be used as an antiseptic, disinfectant, and has pesticide properties. Oxyquinoline is also a chelating agent which has been used for the quantitative determination of metal ions.

Decitabine (5-aza-2'-deoxycytidine or 5-Aza-Cdr) is a cytosine analogue that was first synthesized in the early 1960s by Pliml and Sorm and is currently marketed as Dacogen® by Eisai (Tokyo, Japan). It differs from deoxycytidine by the substitution of nitrogen for carbon at the 5-position of the pyrimidine ring. It was noted to have an antileukemic effect in cell lines, with more potency in vitro than cytarabine. Initially, its cytotoxicity was attributed to its ability to impair DNA synthesis and cause DNA damage similar to other antimetabolites. At low doses, decitabine induces differentiation by reversing DNA methylation-induced gene silencing. Once inside a cell, decitabine is phosphorylated and activated by the enzyme deoxycytidine kinase to its triphosphate form aza-dCTP. It then competes with and replaces cytosine in the CpG (cytosine-guanosine dinucleotide) islands that occur in clusters in promoter regions. During subsequent cell divisions, aza-dCTP inhibits methylation of the promoter by forming a covalent bond with the enzyme DNA methyltransferase (DNMT), and thereby traps and contributes to degradation of the enzyme.

Chlorambucil and Cisplatin are alkylating agents used to treat cancer. Chlorambucil is in the class of nitrogen mustards, and Cisplatin is a platinum based-agent. Chlorambucil produces its anti-cancer effects by interfering with DNA replication and damaging the DNA in a cell. The DNA damage induces cell cycle arrest and cellular apoptosis via the accumulation of cytosolic p53 and subsequent activation of Bcl-2-associated X protein, an apoptosis promoter. Cisplatin crosslinks DNA in several different ways, interfering with cell division by mitosis. The damaged DNA elicits DNA repair mechanisms and activates apoptosis.

Vincristine is a chemotherapy drug that belongs to a group of drugs called vinca alkaloids. Vincristine works by stopping the cancer cells from separating into 2 new cells. Vincristine works partly by binding to the tubulin protein, stopping the tubulin dimers from polymerizing to form microtubules, causing the cell to be unable to separate its chromosomes during the metaphase. The cell then undergoes apoptosis.

Letrozole is an aromatase inhibitor which is used in the treatment of hormonally-responsive breast cancer after surgery. Letrozole is also for ovulation induction. Letrozole blocks the production of estrogens in this way by competitive, reversible binding to the heme of its cytochrome P450 unit. Letrozole has shown to reduce estrogen levels by 98 percent while raising testosterone levels.

Tretinoin is a derivative of vitamin A. It is used on the skin (topically) in the treatment of mild to moderate acne and on skin that has been damaged by excessive exposure to the sun. Tretinoin irritates the skin and causes the cells of the skin to grow (divide) and die more rapidly, increasing the turnover of cells. Tretinoin can also induce acute promyelocytic leukemia cells to differentiate and stops them from proliferating; in people there is evidence that it forces the primary cancerous promyelocytes to differentiate into their final form.

Estradiol is the main circulating oestrogen in women and reaches a plasma concentration of 30-400 pg/mL before menopause. Estradiol regulates growth and the development of the reproductive system, also, helps to maintain the osseous tissue, the central nervous system and the vasodilatation in the vascular tissue. The protective effect of Estradiol in the vasculature and against cardiovascular disease (CVD) has been demonstrated in several hormone replacement studies. Estradiol activates BK channels via a process that requires the presence of the β1 subunit. Valverde et al. were the first to propose that Estradiol affected BK channels by binding to β1, but it is still a matter of debate whether the agonistic action of Estradiol on BK channels is caused by its binding to the β1 subunit or to the α/β1 complex. Moreover, the molecular nature of the Estradiol binding site and the mode of action of the hormone are at present unknown. Acute application of Estradiol (100 nM) decreases smooth muscle excitability by activating BK channels. Notably, Estradiol or its membrane-impermeant form (E2-BSA) can induce a fast increase in BK channel activity in MCF-7 breast epithelial cancer cells with an EC50 of 80 pM reaching a maximal effect at 10 nM34. Rapid effects of Estradiol have also been reported in neurons of the area postrema where nanomolar concentrations of E2 can decrease the firing rate most probably by increasing BK current35. All these examples underscore the physiological importance of the regulation of BK channels by E2 and made worthwhile efforts in determining the molecular nature of the interaction between this hormone and the BK channel.

Cyclosporine has been a core component of immunosuppression in both immune dysregulatory disorders and organ transplantation. For immune disorders involving ophthalmologic, dermatologic, hematologic, gastroenterologic, neurologic, or musculoskeletal systems, cyclosporine has demonstrated marked efficacy in relieving clinical symptoms and reversing pathological developments. Additionally, after the drug's implementation in transplantation medicine, rates of acute rejection and one-year graft survival have improved dramatically.

Methotrexate is a chemotherapy agent and immune system suppressant. It is used to treat cancer, autoimmune diseases, ectopic pregnancy, and for medical abortions. Types of cancers it is used for include breast cancer, leukemia, lung cancer, lymphoma, and osteosarcoma. Types of autoimmune diseases it is used for include psoriasis, rheumatoid arthritis, and Crohn's disease. It can be given by mouth or by injection. Methotrexate is an antimetabolite of the antifolate type. It is thought to affect cancer and rheumatoid arthritis by two different pathways. For cancer, methotrexate competitively inhibits dihydrofolate reductase (DHFR), an enzyme that participates in the tetrahydrofolate synthesis. The affinity of methotrexate for DHFR is about 1000-fold that of folate. DHFR catalyses the conversion of dihydrofolate to the active tetrahydrofolate. Folic acid is needed for the de novo synthesis of the nucleoside thymidine, required for DNA synthesis. Also, folate is essential for purine and pyrimidine base biosynthesis, so synthesis will be inhibited. Methotrexate, therefore, inhibits the synthesis of DNA, RNA, thymidylates, and proteins. For the treatment of rheumatoid arthritis (immune suppression), multiple mechanisms appear to be involved, including the inhibition of enzymes involved in purine metabolism, leading to accumulation of adenosine; inhibition of T cell activation and suppression of intercellular adhesion molecule expression by T cells; selective down-regulation of B cells; increasing CD95 sensitivity of activated T cells; and inhibition of methyltransferase activity, leading to deactivation of enzyme activity relevant to immune system function. Another mechanism of MTX is the inhibition of the binding of interleukin 1-beta to its cell surface receptor.

Troglitazone is an antidiabetic and anti-inflammatory drug, and a member of the drug class of the thiazolidinediones. Troglitazone is an oral antihyperglycemic agent which acts primarily by decreasing insulin resistance. Troglitazone is used in the management of type II diabetes. Troglitazone binds to nuclear receptors (PPAR) that regulate the transcription of a number of insulin responsive genes critical for the control of glucose and lipid metabolism. Troglitazone decrease nuclear factor kappa-B (NF-κB) and increase its inhibitor (IκB).

Azathioprine is a purine analogue with cytotoxic and immunosuppressive activity. Azathioprine is a prodrug that is converted by hepatic xanthine oxidase to its active metabolite 6-mercaptopurine (6-MP). 6-MP is further metabolized by hypoxanthine-guanine phosphoribosyltransferase (HGPRT) into 6-thioguanosine-5'-phosphate (6-thio-GMP) and 6-thioinosine monophosphate (6-thio-IMP), both inhibit nucleotide conversions and de novo purine synthesis. This leads to inhibition of DNA, RNA, and protein synthesis. As a result, cell proliferation may be inhibited, particularly in lymphocytes and leukocytes. Azathioprine an immunosuppressive agent in organ transplantation to prevent rejection and in autoimmune diseases as a corticosteroid sparing agent.

Quercetin, a flavonoid found in fruits and vegetables, has unique biological properties that may improve mental/physical performance and reduce infection risk. These properties form the basis for potential benefits to overall health and disease resistance, including anti-carcinogenic, anti-inflammatory, antiviral, antioxidant, and psychostimulant activities, as well as the ability to inhibit lipid peroxidation, platelet aggregation and capillary permeability, and to stimulate mitochondrial biogenesis. Quercetin is a naturally occurring polar auxin transport inhibitor. Quercetin inhibits lipopolysaccharide (LPS)-induced tumor necrosis factorα (TNF-α) production in macrophages and LPS-induced IL-8 production in lung A549 cells. Moreover, in glial cells it was even shown that quercetin can inhibit LPS-induced mRNA levels of TNF-α and interleukin IL-1α, this effect of quercetin resulted in a diminished apoptotic neuronal cell death induced by microglial activation. Quercetin inhibits production of inflammation-producing enzymes (cyclooxygenase (COX) and lipoxygenase (LOX)). It limits LPS-induced inflammation via inhibition of Src- and Syk-mediated phosphatidylinositol-3-Kinase (PI3K)-(p85) tyrosine phosphorylation and subsequent Toll Like Receptor 4 (TLR4)/MyD88/PI3K complex formation that limits activation of downstream signaling pathways in RAW 264.7 cells. It can also inhibit FcεRI-mediated release of pro-inflammatory cytokines, tryptase and histamine from human umbilical cord blood-derived cultured mast cells (hCBMCs); this inhibition appears to involve in inhibition of calcium influx, as well as phospho-protein kinase C (PKC).

Resorcinol is an organic compound with the formula $C_6H_4(OH)_2$. Resorcinol is used as an antiseptic and disinfectant in topical pharmaceutical products in the treatment of skin disorders and infections such as acne, seborrheic dermatitis, eczema, psoriasis, corns, calluses, and warts. It is also used to treat corns, calluses, and warts. It exerts a keratolytic activity.

Agents that reduce expression of CXCR3 (the receptor for MIG) include, for example, formaldehyde and taurine. Agents that are antagonists for CXCR3 include, for example, piperazinyl-piperidines (e.g., SCH546738), 8-azaquinazolinones (e.g., AMG 487), 3-phenyl-3H-quinazolin-4-ones, aryl piperazine, 4-aryl-5-piperazinylthiazoles, arylpiperazines, benzetimide derivatives, imidazolidines, imidazolium, lysergic acid derivative, diaminocyclobutenediones, zinc phthalocyanine, and NBI-74330. (See Andrews et al., J. Med. Chem. 59:2894-917 (2016), which is incorporated by reference in its entirety for all purposes). Chemical structures for specific antagonists of CXCR3 are found in Andrews 2016, and are hereby incorporated by reference in their entirety for all purposes. A few of the specific structures are shown below:

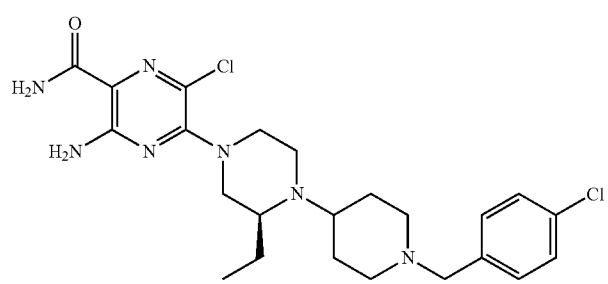

1 (SCH 546738)

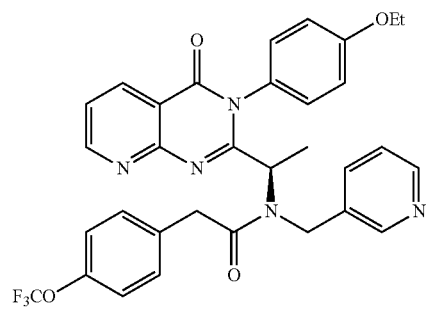

2 (AMG 487)

CXCR3 ANTAGONISTS
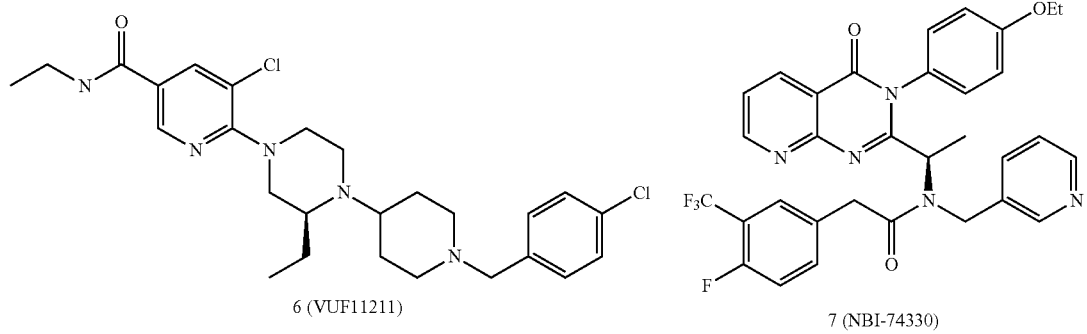
6 (VUF11211)
7 (NBI-74330)
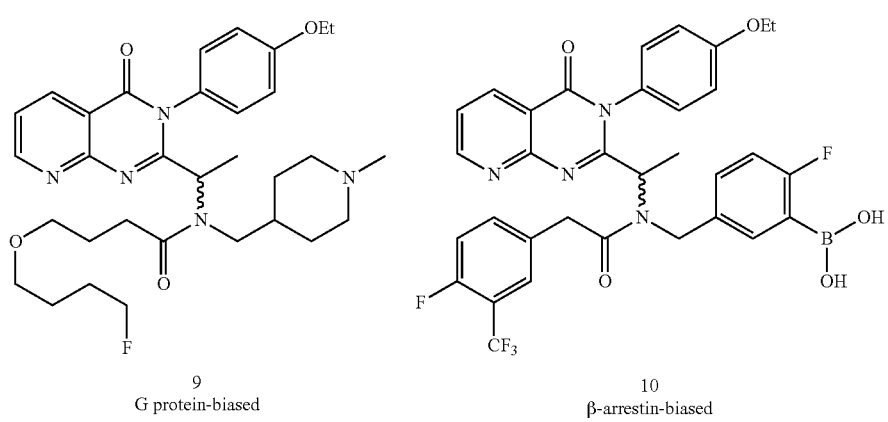
9
G protein-biased
10
β-arrestin-biased
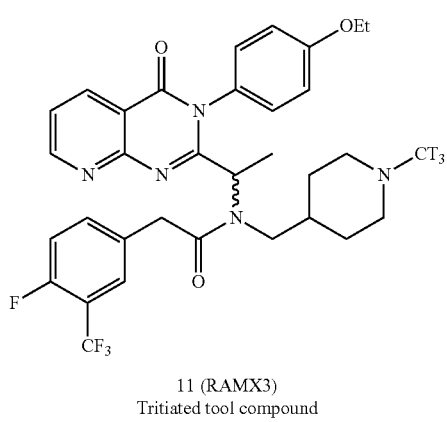
11 (RAMX3)
Tritiated tool compound
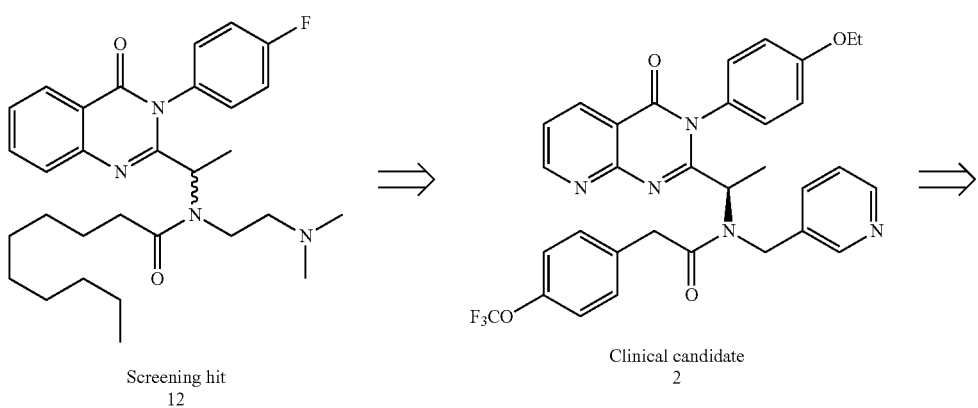
Screening hit
12
Clinical candidate
2

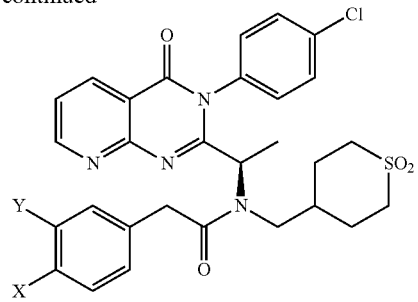
Possible back-ups
13 (X = F, Y = CF₃) 14 (X = CF₃, Y = F)
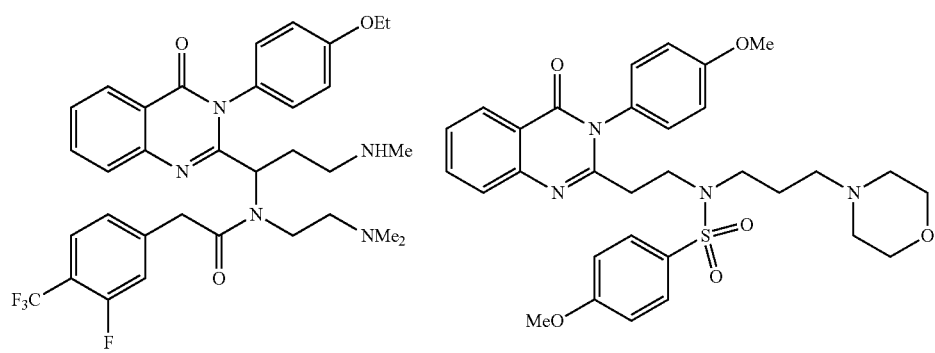
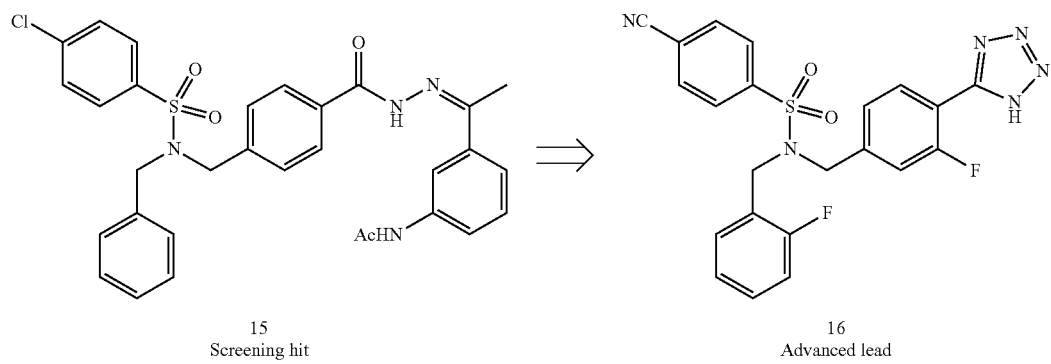
15
Screening hit
16
Advanced lead
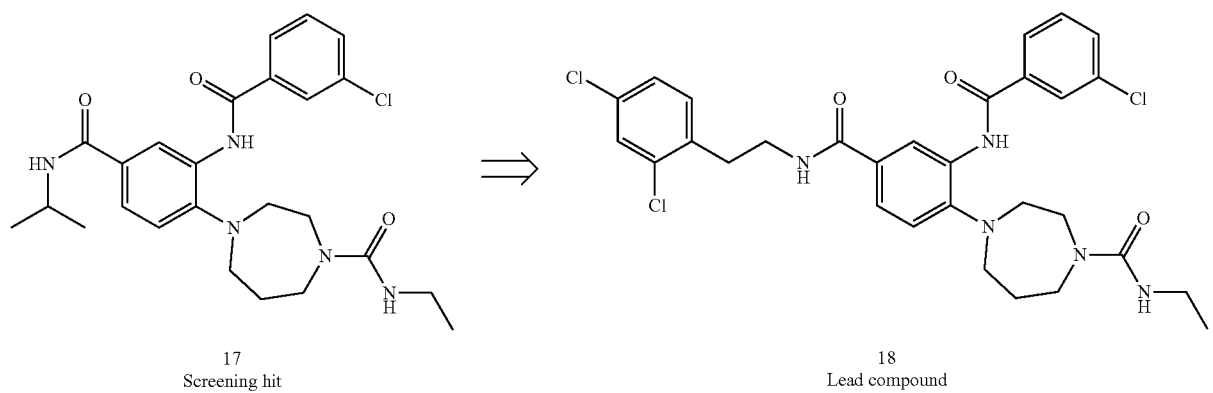
17
Screening hit
18
Lead compound

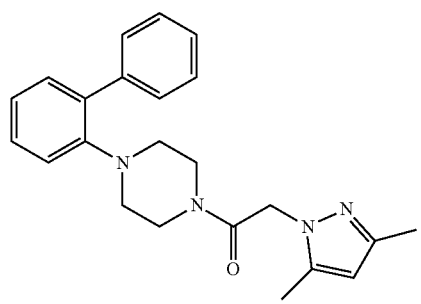
19
Singleton hit
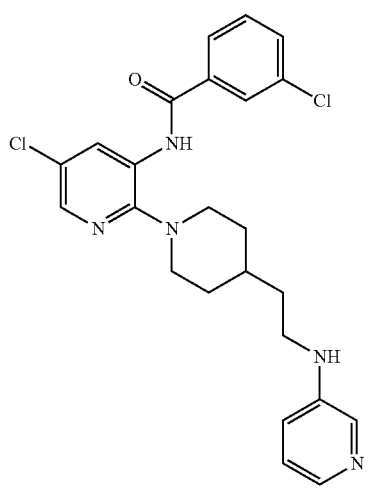
20
pIC$_{50}$ 8.7 (Ca$^{2+}$ flux)
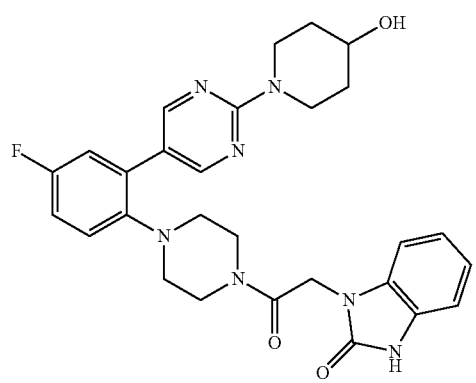
21
pIC$_{50}$ 6.0 (Ca$^{2+}$ flux)
pIC$_{50}$ 7.7 (chemotaxis)
hERG pIC$_{50}$ <4.5
solubility >53 μg/mL
replacement with 4-
methoxyphenyl:
pIC$_{50}$ 7.0
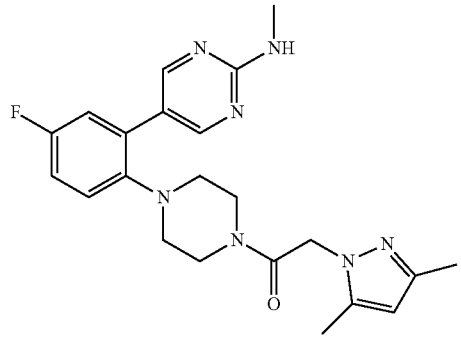
22
in vivo rat PK
(2 mg/kg po)
AUC 271 ng*h/mL
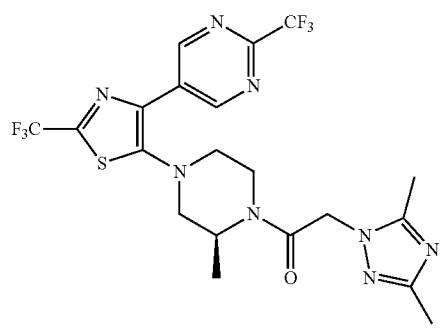
24 halogens preferred; 2,4-dichloro best

•m-Cl favoured
•carboxylic acid or ester tolerated
•benzene can be replaced by thiophene tolerates substitution on chain

•piperazine distinguishes series from Ligand Pharmaceuticals' homopiperizines

•small basic group essential

•carbonyl not essential

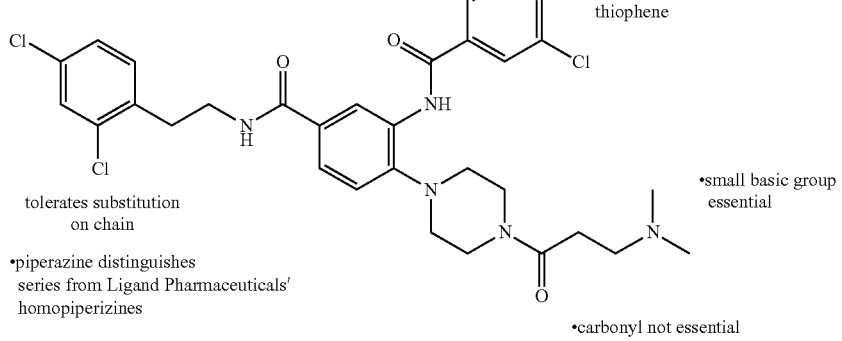

25

•trans more active than cis across cHex
•oPent and oBu acids also active p-Cl most usual stereochemistry usually important but varies depending on benzylic group ether most usual Me and Cl also used in place of OMe succinimide most usual

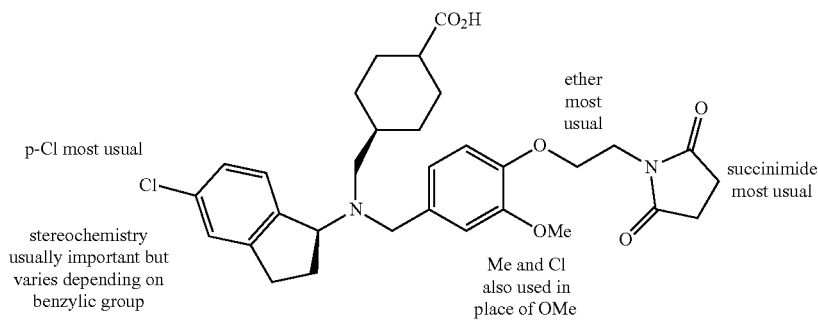

26 many example have p-Cl, m-F small alkyl preferred, usually nPr, tBu, CH₂-cycloalkyl, Et appears too small α-amino acid analogues are less active

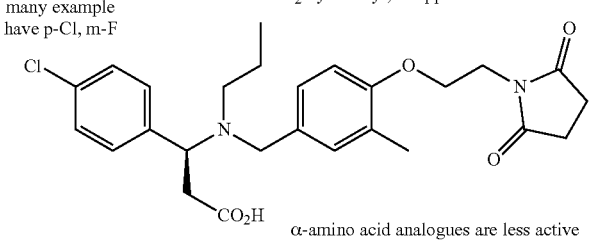

27

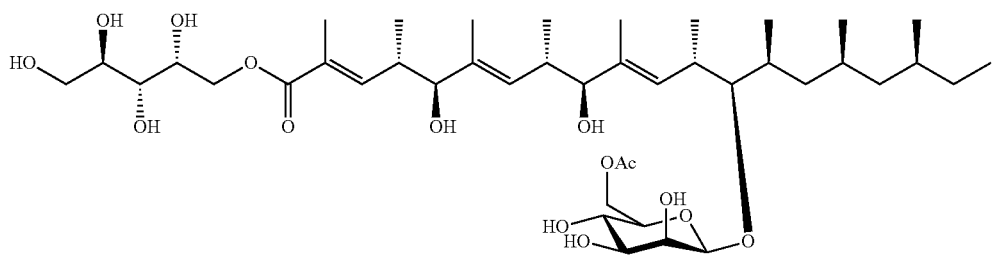

28
pIC$_{50}$ 4.8 ($^{128}$I-CXCL10)

-continued
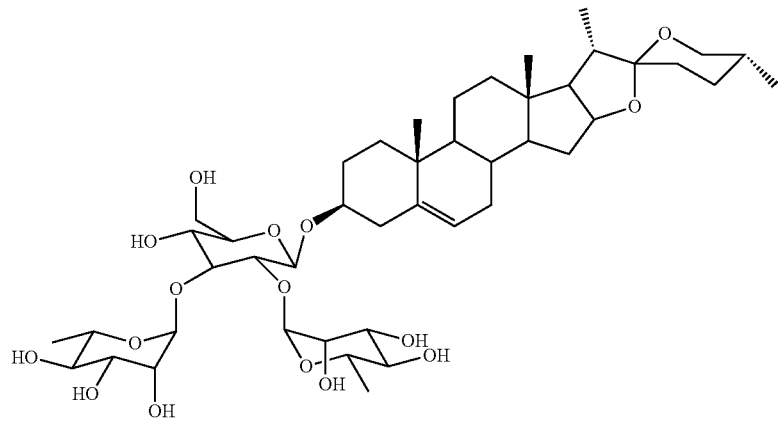
29
pIC$_{50}$ 6.3 ($^{128}$I-CXCL10)
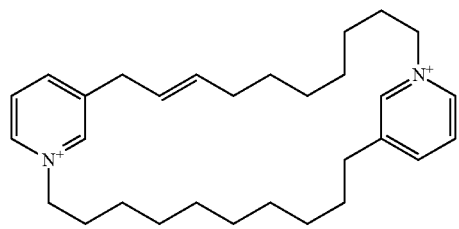
30
pIC$_{50}$ 6.2 ($^{128}$I-CXCL10)
1. PYRIDINE SUB-SERIES
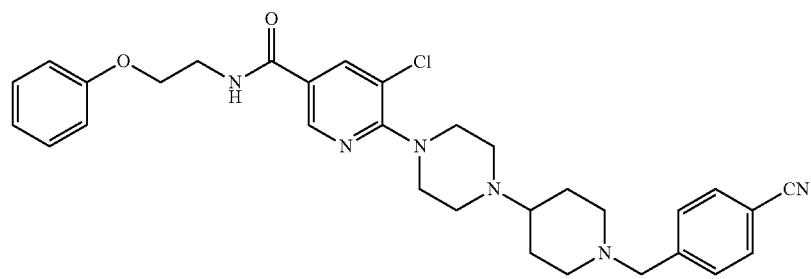
32
HTS hit
pK$_I$ 7.0 ($^{128}$I-CXCL10)
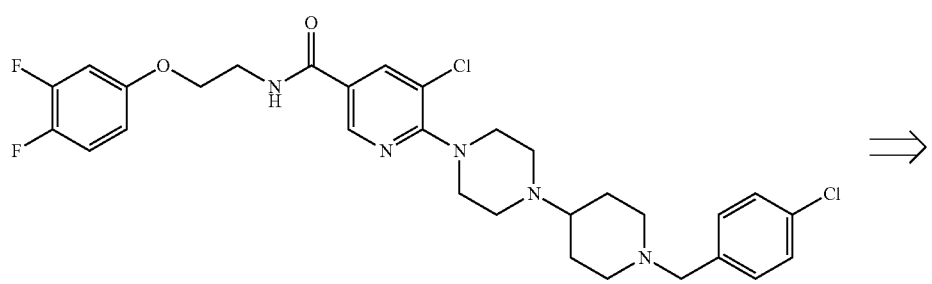
33

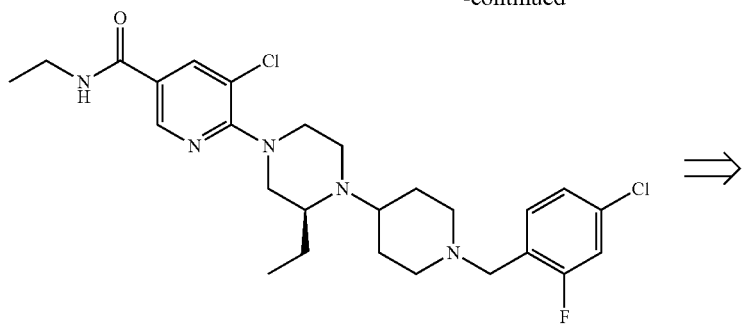
34
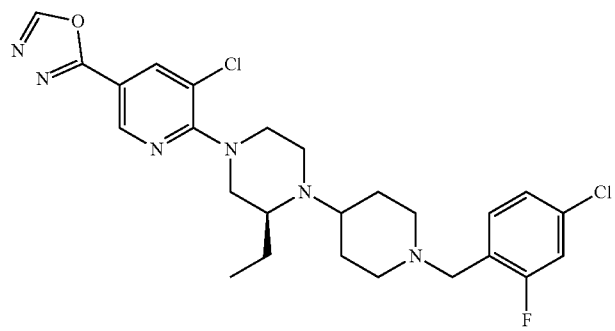
35
2. PYRAZINE SUB-SERIES
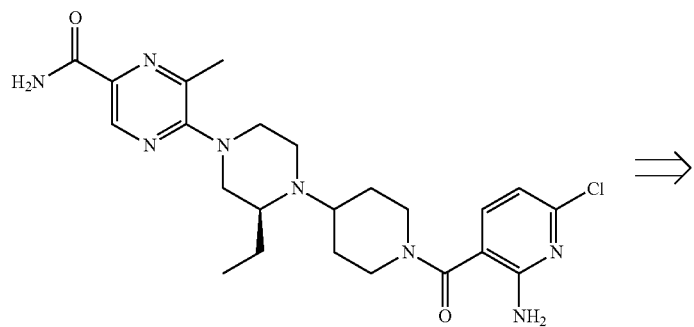
36
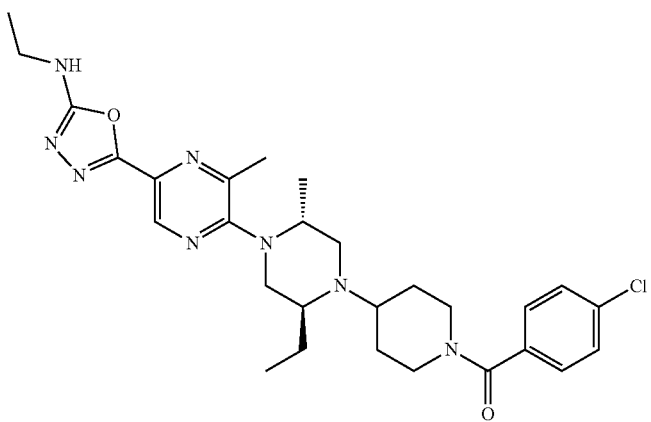
31 (SCH 900875)

-continued
DAICHI SANKYO
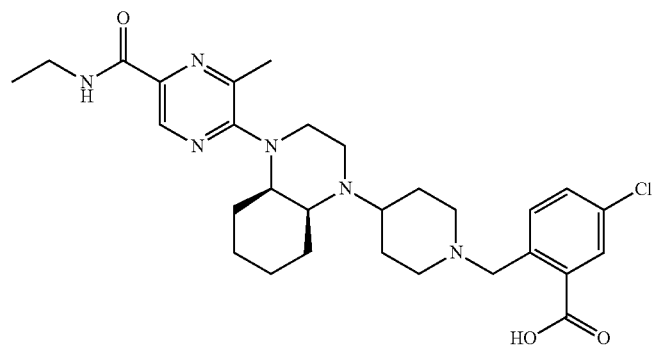
37
JOHNSON & JOHNSON
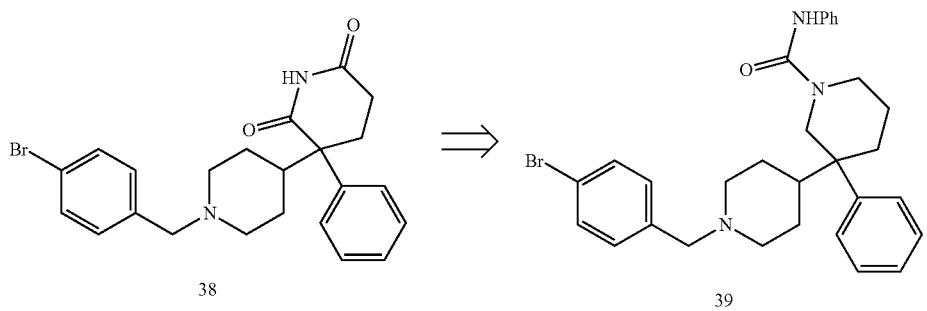
38 39
ONO
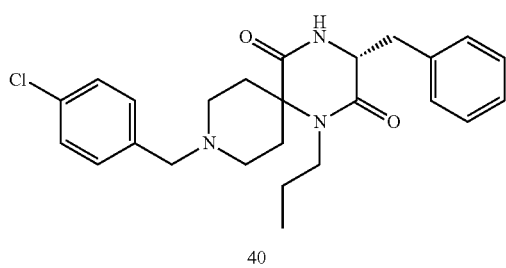
40
VU UNIVERSITY AMSTERDAM
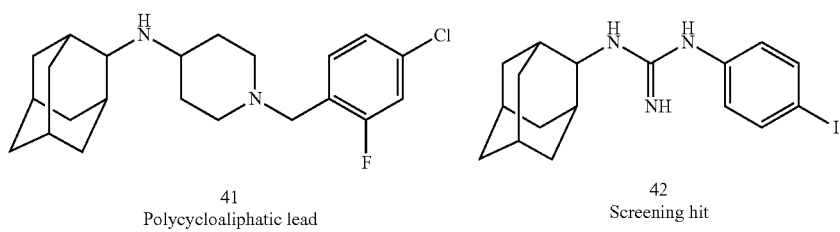
41
Polycycloaliphatic lead
42
Screening hit
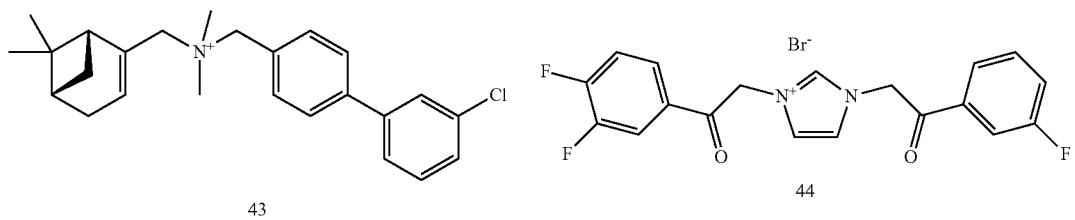
43 44

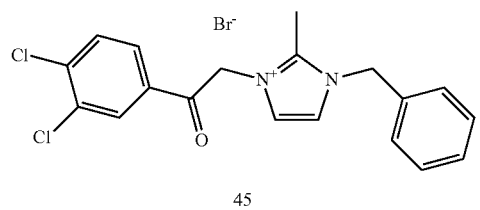
45
GLAXOSMITHKLINE
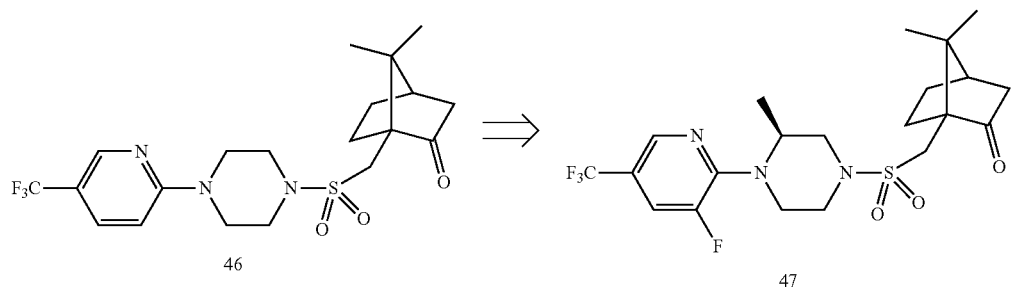
46   47
ABBOTT LABORATORIES
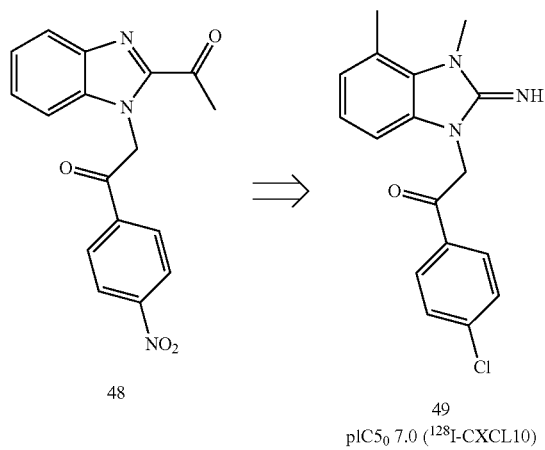
48   49
pIC$_{50}$ 7.0 ($^{128}$I-CXCL10)
SEOUL NATIONAL UNIVERSITY
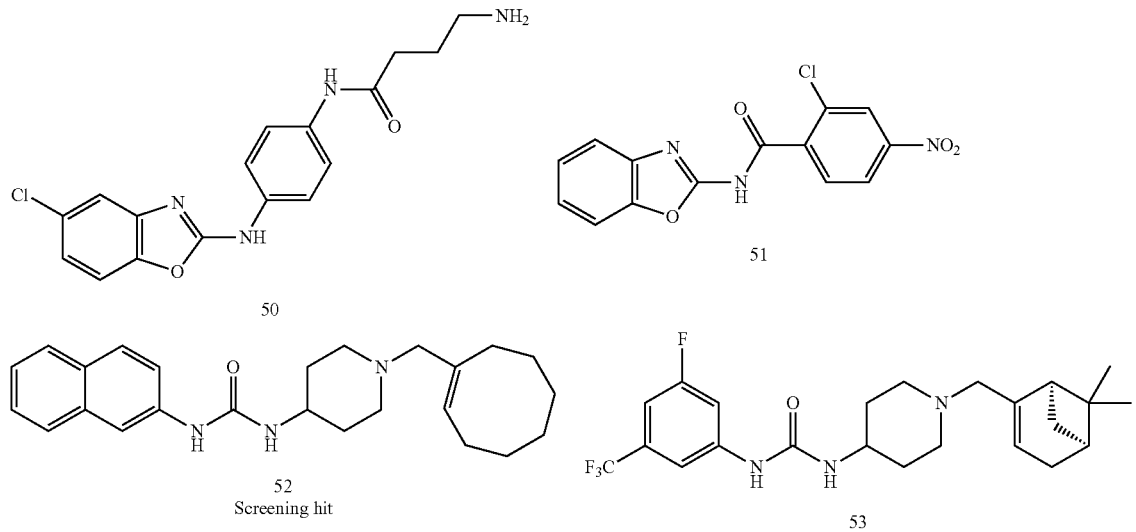
50
51
52
Screening hit
53

-continued
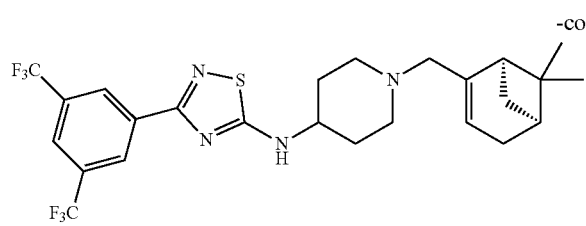
54
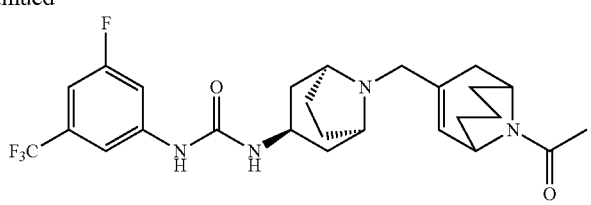
55
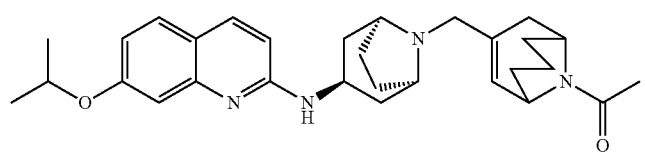
56
NOVARTIS
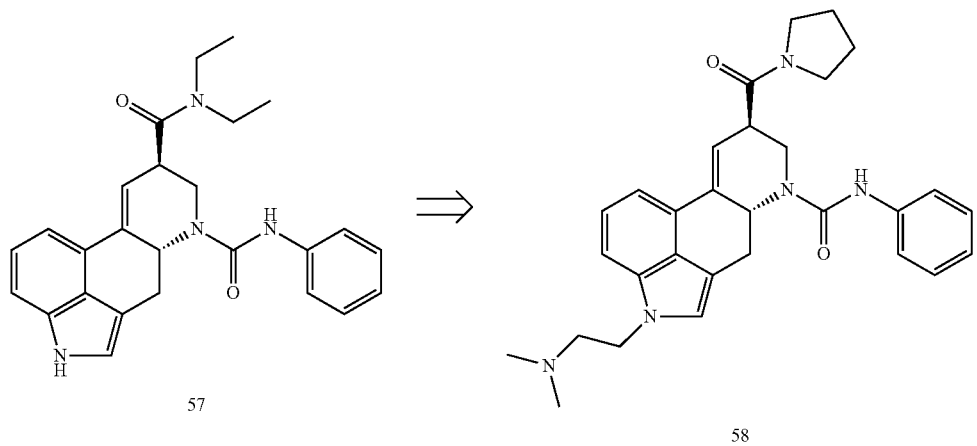
57    58
GALDERMA RESEARCH & DEVELOPMENT
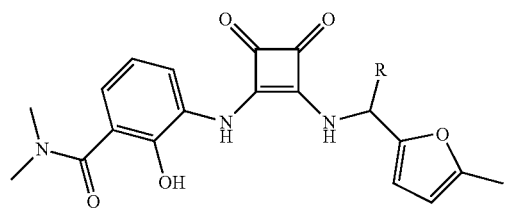
59 (SCH 527123): R = Et
(CXCR1/CXCR2 ligand developed by
Schering Plough)
60: R = 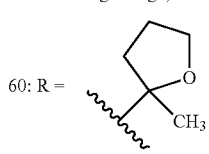
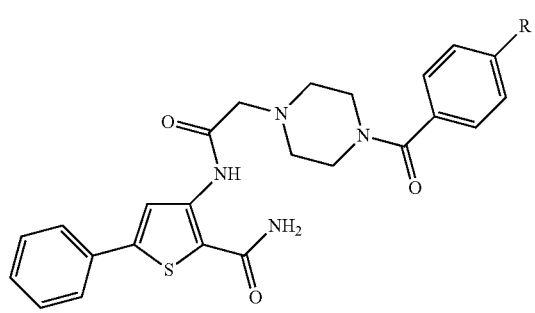
61: R = Me

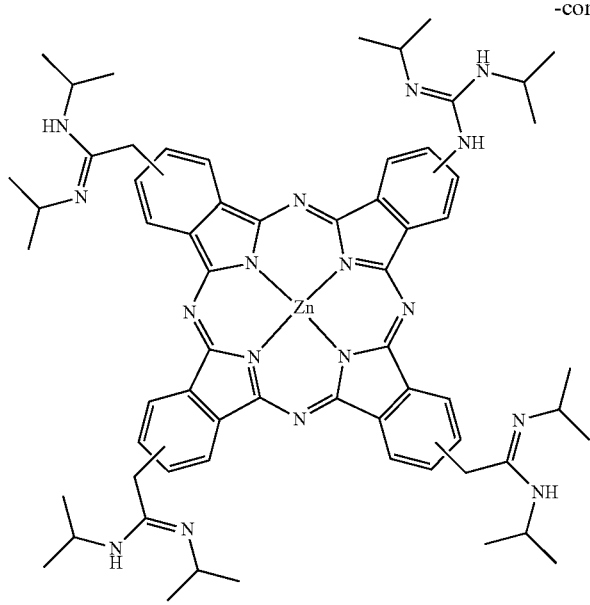

62

Other small molecule antagonists are found, for example, in US20060036093, WO2009/105435, which all are incorporated by reference in their entirety for all purposes.

Any of the foregoing antibodies or fragments thereof (collectively antibodies) can be engineered for use in humans by methods such as, for example, chimerization, humanization, humaneering, etc, which are known in the art.

In addition, any of the foregoing antibodies or fragments thereof (collectively antibodies) can include a protracting moiety that extends a half-life ($T_{1/2}$) or/and the duration of action of the antibody. The protracting moiety can extend the circulation $T_{1/2}$, blood $T_{1/2}$, plasma $T_{1/2}$, serum $T_{1/2}$, terminal $T_{1/2}$, biological $T_{1/2}$, elimination $T_{1/2}$ or functional $T_{1/2}$, or any combination thereof, of the antibody. One or more protracting moieties can be combined (covalently or non-covalently) with an antibody. Protracting moieties include, for example, hydrophilic polymers (e.g., PEG, dextran, etc.), a synthetic polymer, glycosylation, human serum albumin (HSA) or a portion thereof (e.g., domain III) that binds to the neonatal Fc receptor (FcRn), or a carboxy-terminal peptide (CTP).

Cardiovascular Disease

Cardiovascular disease include a class of diseases that involve the heart, the blood vessels (arteries, capillaries, and veins) or both. Cardiovascular disease refers to any disease that affects the cardiovascular system, principally cardiac disease including cardiomyopathies, vascular diseases of the brain and kidney, and peripheral arterial disease. Cardiovascular disease can refer to a disease that primarily affects the heart, and can be referred to as cardiac disease. Cardiovascular disease can refer to a disease in which the pathology begins with cardiac damage, malfunction, or malformation, as opposed to disease in which cardiac damage, malfunction, or malformation is a result of a primary pathology present at a site remote from the heart (e.g., cardiovascular disease as a comorbidity to another disease or condition). For example, heart failure, cardiac dysrhythmias (abnormalities of heart rhythm including increased QT duration and atrial flutter and/or fibrillation), inflammatory heart disease including endocarditis (inflammation of the inner layer of the heart, the endocardium, most commonly the heart valves); inflammatory cardiomegaly (enlarged heart, cardiac hypertrophy); myocarditis (inflammation of the myocardium); valvular heart disease; congenital heart disease; and rheumatic heart disease (heart muscle and valve damage due to rheumatic fever caused by streptococcal bacteria infections) are examples of cardiac damage, malfunction, or malformation in which the primary pathology can be or is present in the heart, and subsequently can result in vascular or other systemic disease. Alternatively, coronary heart disease (also ischaemic heart disease or coronary artery disease); hypertensive heart disease (diseases of the heart secondary to high blood pressure); cor pulmonale (failure at the right side of the heart with respiratory system involvement); cerebrovascular disease (disease of blood vessels that supplies to the brain such as stroke); peripheral arterial disease (disease of blood vessels that supplies to the arms and legs); and artherosclerosis are a result of pathology present initially at a site remote from the heart. Cardiovascular disease initiated either at the heart or at a site remote from the heart can result in heart failure. Cardiovascular disease can include disease in which the initial pathology is at a site remote from the heart. Cardiovascular disease also includes conditions affecting the heart, heart valves, and vasculature (e.g., arteries and veins) of the body and encompasses diseases and conditions including, but not limited to arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

Cardiomyopathy includes one or more conditions (e.g., 1, 2, 3, 4, 5, 6, 7, 8, 9, 10, or more of) selected from the group consisting of increased QT duration, arrhythmias, myocardial ischemia, hypertension and thromboembolic complications, myocardial dysfunction, cardiomyopathy, heart failure, atrial fibrillation, cardiomyopathy and heart failure, heart failure and LV dysfunction, atrial flutter and fibrillation, and, heart valve damage and heart failure. In certain embodiments, cardiomyopathy does not include cardiomyopathy as a comorbidity to another disease or condition.

Heart failure often called congestive heart failure (CHF) or congestive cardiac failure (CCF), includes conditions that occur when the heart is unable to provide sufficient pump action to maintain blood flow to meet the needs of the body. Heart failure can cause a number of symptoms including shortness of breath, leg swelling, and exercise intolerance. The condition is typically diagnosed by patient physical examination and confirmed with echocardiography. Common causes of heart failure include myocardial infarction and other forms of ischemic heart disease, hypertension, valvular heart disease, and cardiomyopathy.

Cardiovascular disease includes atherosclerosis a chronic disease process characterized by lipid deposits and fibrosis of the intima, irregularly distributed in large and medium sized arteries. The disease is progressive and most often becomes clinically manifest in the middle-aged and elderly. When severe, the atherosclerotic plaque causes a reduction of the cross-sectional area of the arterial lumen, with and without thrombosis. Atherosclerotic plaques can occur in essentially any or all of the blood vessels of the body, resulting in cardiovascular diseases involving the heart (e.g., acute coronary syndrome, heart failure, and myocardial infarction), the brain (e.g., stroke, transient ischemic attack, and brain infarction), the kidney (e.g., acute and chronic kidney disease, hypertension), and the extremities (e.g., peripheral vascular disease, lower and/or upper extremity claudication, and lower and/or upper extremity ischemia). Resultant ischemic manifestations include: angina pectoris, rayocardial infarction, stroke, intermittent claudication, gangrene of the lower extremities, and renovascular hypertension. Atherosclerosis can be considered to be an inflammatory disease. For example, the lesions of atherosclerosis appear to represent a series of highly-specific cellular and molecular responses that can be described as an inflammatory disease. See, e.g., Ross, "Atherosclerosis—An inflammatory disease" N Engl J Med (1999), 340:115-126; the publications cited in Ross (1999); and subsequent publications that cite Ross (1999); each of which is incorporated herein in reference in its entirety.

A subject can be identified as having cardiovascular disease by the presence of any one of: documented coronary artery disease, documented cerebrovascular disease, documented carotid disease, documented peripheral arterial disease, or combinations thereof. A subject can also be identified as having cardiovaswcular disease if the subject is at least 45 years old and: (a) has one or more stenosis of greater than 50% in two major epicardial coronary arteries; (b) has had a documented prior MI; (c) has been hospitalized for high-risk NSTE ACS with objective evidence of ischemia (e.g., ST-segment deviation and/or biomarker positivity); (d) has a documented prior ischemic stroke; (e) has symptomatic artery disease with at least 50% carotid arterial stenosis; (0 has asymptomatic carotid artery disease with at least 70% carotid arterial stenosis per angiography or duplex ultrasound; (g) has an ankle-brachial index ("ABI") of less than 0.9 with symptoms of intermittent claudication; and/or (h) has a history of aorto-iliac or peripheral arterial intervention (catheter-based or surgical).

Cardiovascular Treatments Using iAge and Cardiac Markers

Subjects with cardiovascular disease or at risk for cardiovascular disease have their blood drawn and an iAge, CRS, cardiac marker levels (MIG, LIF, SIRT3), and cAge are calculated as described above. If the subject's iAge, CRS, cardiac marker levels (MIG, LIF, SIRT3), and/or cAge places them in the youngest quartile for their age group they can be classified as low risk for cardiovascular disease and move forward with the standard therapy (CVD patients) or no therapy (patients at risk but no CVD at the time). If the subject's iAge, CRS, cardiac marker levels (MIG, LIF, SIRT3), and/or cAge places them in the middle two quartiles, the subject's blood cells (e.g., CD4+ and CD8+ cells) can be tested for Jak-STAT activity (see, e.g., Example 1 below). Subject's whose Jak-STAT activity places them in the highest quartile can be classified as low risk and move forward with standard therapy (CVD patients) or no therapy (patients at risk but no CVD at the time). Subjects whose Jak-STAT activity places them in the lower three quartiles can be classified as higher risk for cardiovascular disease and can be treated to lower iAge, CRS, cardiac marker levels (MIG, LIF, SIRT3), and/or cAge (and increase their Jak-STAT score) into a low risk group. If the subject's iAge, CRS, cardiac marker levels (MIG, LIF, SIRT3), and/or cAge places them in the oldest quartile, they can be classified as higher risk patients and can be treated to lower their iAge, CRS, cardiac marker levels (MIG, LIF, SIRT3), and/or cAge (see above) into a low risk group.

Alternatively, if the subject's iAge, CRS, cardiac marker levels (MIG, LIF, SIRT3), and/or cAge places them in the youngest iAge, CRS, cardiac marker levels (MIG, LIF, SIRT3), and/or cAge quintile for their age group (see Table 1) they can be classified as low risk and move forward with the standard therapy (CVD patients) or no therapy (patients with no CVD at the time). If the subject's iAge, CRS, cardiac marker levels (MIG, LIF, SIRT3), and/or cAge places them in the middle three quintiles, the subject's blood cells (e.g., CD4+ and CD8+ cells) are stimulated and Jak-STAT activity is measured (see, e.g., Example 1 below). Subject's whose Jak-STAT activity places them in the highest quartile can be classified as low risk and move forward with the standard therapy (CVD patients) or no therapy (patients at risk but no CVD at the time). Subjects whose Jak-STAT activity places them in the lower three quartiles can be classified as higher risk and can be treated to lower iAge, CRS, cardiac marker levels (lower MIG, raise LIF, raise SIRT3), and/or cAge (and increase their Jak-STAT score) into a low risk group. If the subject's iAge places them in the oldest quintile, they can be classified as higher risk and can be treated to lower their iAge, CRS, cardiac marker levels (lower MIG, increase LIF, increase SIRT3), and/or cAge (see above) into a low risk group of a younger iAge quintile.

Still alternatively, if the subject's iAge, CRS, cardiac marker levels (MIG, LIF, SIRT3), and/or cAge places them in the youngest iAge tertile for their age group (see Table 1) they can be classified as low risk and move forward with the standard therapy (CVD patients) or no therapy (patients at risk but no CVD at the time). If the subject's iAge, CRS, cardiac marker levels (MIG, LIF, SIRT3), and/or cAge places them in the middle tertile, the subject's blood cells (e.g., CD4+ and CD8+ cells) are stimulated and Jak-STAT activity is measured (see, e.g., Example 1 below). Subject's whose Jak-STAT activity places them in the highest quartile can be classified as low risk and move forward with the standard therapy (CVD patients) or no therapy (patients at risk but no CVD at the time). Subjects whose Jak-STAT activity places them in the lower three quartiles can be classified as higher risk and can be treated to lower iAge, CRS, cardiac marker levels (lower MIG, increase LIF, increase SIRT3), and/or cAge (and increase their Jak-STAT score) into a low risk group. If the subject's iAge, CRS, cardiac marker levels (MIG, LIF, SIRT3), and/or cAge places them in the oldest tertile, they can be classified as higher risk and are treated to lower their iAge, CRS, cardiac marker levels (lower MIG, increase LIF, increase SIRT3), and/or cAge (see above) into a low risk group of a younger iAge, CRS, cardiac marker levels (MIG, LIF, SIRT3), and/or cAge tertile.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Figure 1B:
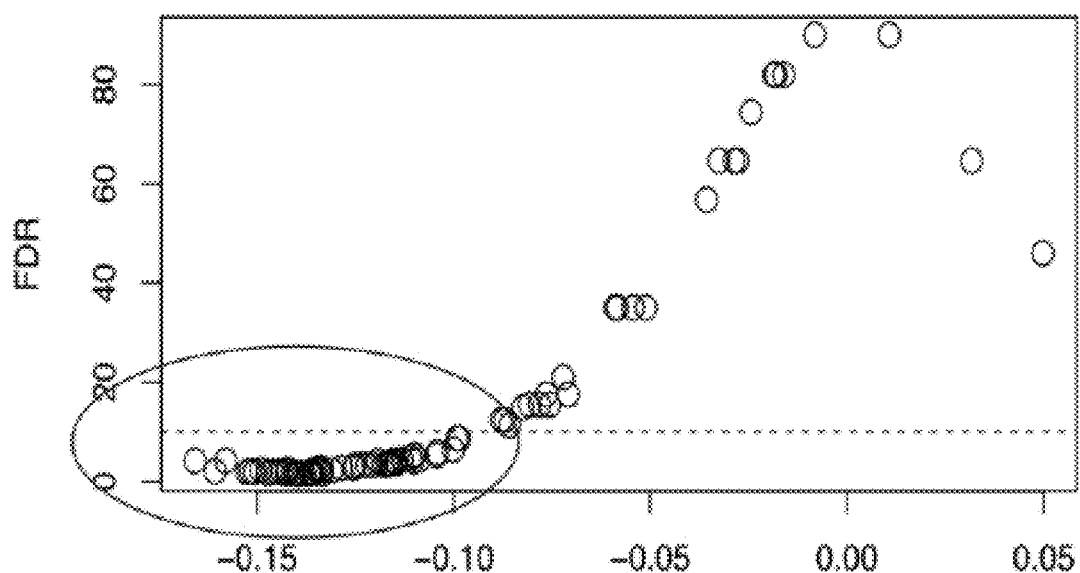
Figure 1C:
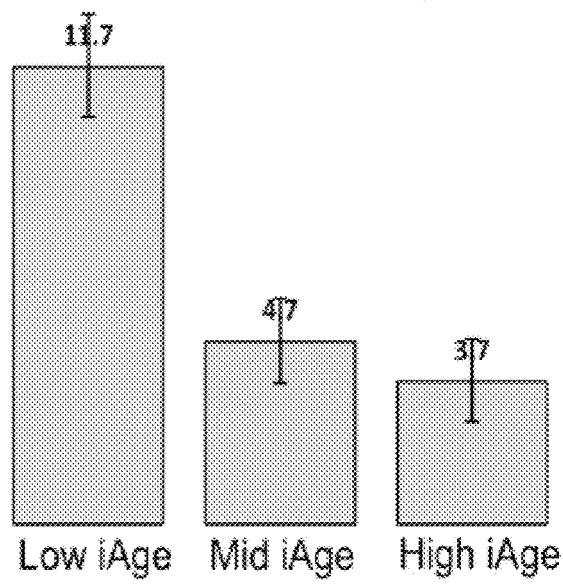

Example 1: iAge Correlates with Naïve CD8(+) T Cells and with the ex vivo Jak-STAT Signaling Responses to Stimulation Data from the Stanford 1 KIP was used to show that frequency of circulating naïve CD8(+) T cells decline with high iAge (A) and that iAge predict poor ex vivo Jak-STAT signaling responses to stimulation (B and C). A total of 96 cytokine-cell-STAT combinations were analyzed with respect of a subject's iAge. These included eight cell types: B cells, CD4(+) T cells (and their CD45(+) and (−) subsets), CD8(+) T cells (and their CD45(+) and (−) subsets), and monocytes; four cytokines: Interleukin-6 (IL-6), IL-10, IL-21 and Interferon-alpha; and three STAT proteins (STAT1, 3 and 5). B: volcano plot, result of a multiple regression analysis with permutation tests to estimate false discovery rates (Benjamini-Hochberg FDR) (y-axis) as a function of the regression coefficients obtained for iAge after adjusting for Age, Gender and cytomegalovirus status. C: normalized ex vivo CD8(+) T cell phosphor-STAT-1 responses to Interleukin-6. The lower tertile for iAge shows significantly more robust responses than the higher tertile for iAge (C). This data is shown in FIG. 1A-C.

iAge is negatively correlated with naive CD8(+) T cells and with the ex vivo Jak-STAT signaling responses to stimulation.

Example 2: Stratification of Cancer Patients Using iAge and CRS

A blood sample is obtained from patients prior to immunotherapy treatment. Serum and immune cells are separated by standard methods. Serum samples are used to measure protein concentration for inflammatory age (iAge) determination; and cells are cytokine-stimulated ex vivo to measure phosphorylation of intracellular signal transducer and activator of transcription (STAT) proteins to derive a cytokine response score (CRS). iAge and CRS can independently predict patient's response to immunotherapy treatment. FIG. 2 shows a flow diagram of this process.

iAge and CRS can be used to stratify cancer patients prior to treatment as responders versus non-responder for immunotherapy.

Example 3: Stratification of Cancer Patients Using iAge iAge can be used to classify cancer patients into responder and non-responders to immunotherapy treatment (A), and to derive iAge individual inflammatory protein signature (barcode), which is fed to iAge personalized recommendation engine to create a individualized initial therapy aimed to reduce iAge, inform medical decision and hence, convert those non-responder patients into responder patients (suitable for immunotherapy) (B). FIG. 3 shows a flow diagram of this process.

iAge is used to stratify patients for cancer immunotherapy and help convert non-responders into responder for immunotherapy.

Example 4: Endothelial Cells Derived from hiPSCs Produce MIG

Human induced pluripotent stem cells (hiPSCs) were obtained from isolated fibroblasts (N=5, in duplicates) using the Yamanaka factors (Takahashi and Yamanaka, 2006) and differentiated them into endothelial cells (hiPSC-ECs) under well-defined conditions as previously described (Hu et al., 2016).

Figure 4:
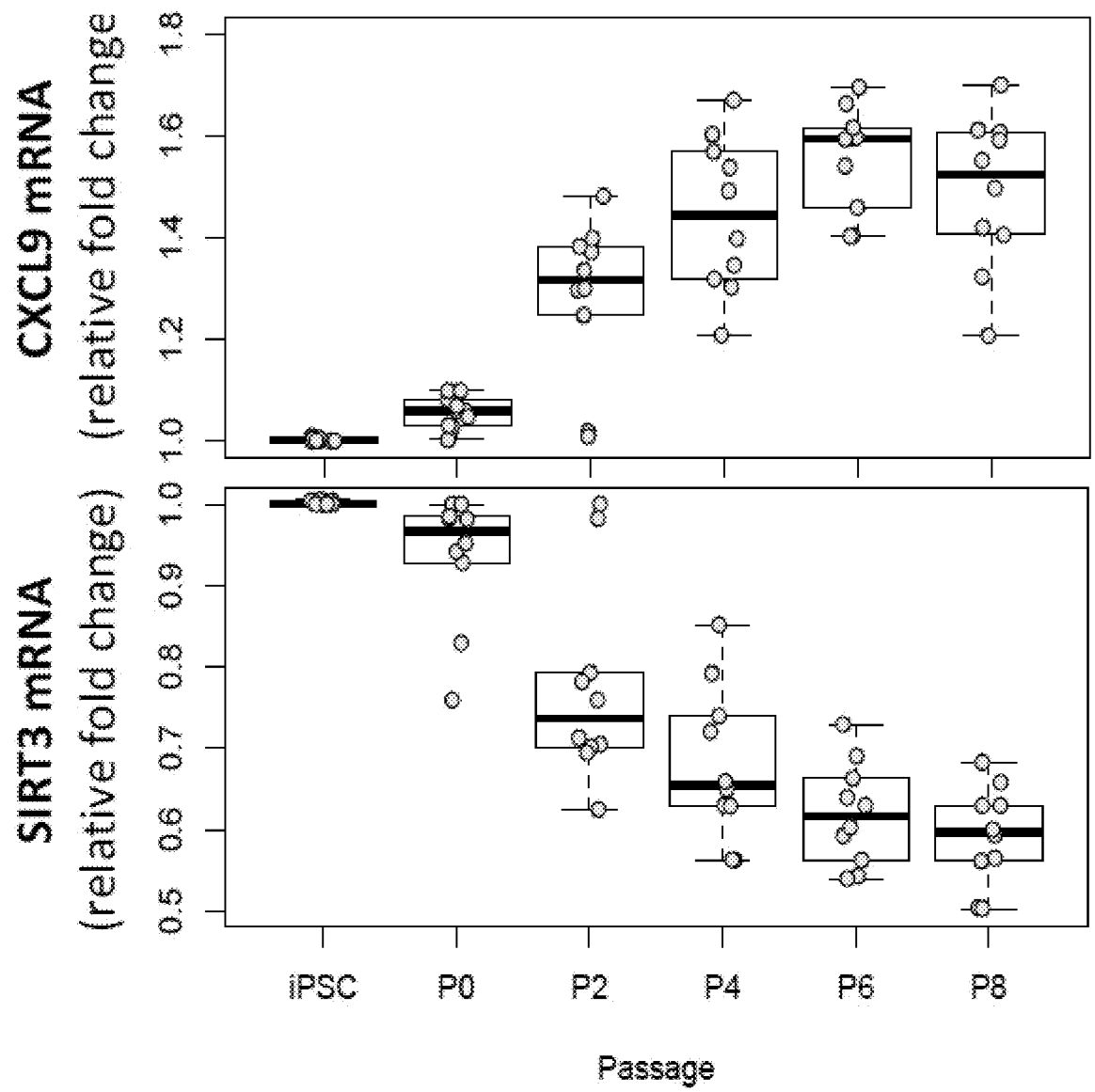
FIG. 4 depicts the fold change in MIG mRNA and SIRT3 mRNA after passage of cells following differentiation into endothelial cells from hiPSCs.

Expression levels of MIG and SIRT3 were measured by RT-PCR. A significant age-dependent increase in MIG mRNA expression levels is observed (P<0.01), which reaches a plateau after the sixth cell passage. (See FIG. 4) Concomitant with the increase in MIG, down-regulation in SIRT3 mRNA can be observed after the second cell passage (P<0.01). (See FIG. 4)

Example 5: Expression of CXCR3 in Endothelial Cells

Human induced pluripotent stem cells were made as described in Example 4. Expression of the MIG receptor, CXCR3, was measured in young cardiomyocytes derived from hiPSCs (hiPSC-CM) as well as in hiPSC-ECs (endothelial cells derived from hiPSC), HUVEC cells, freshly isolated fibroblasts and hiPSCs.

Figure 5:
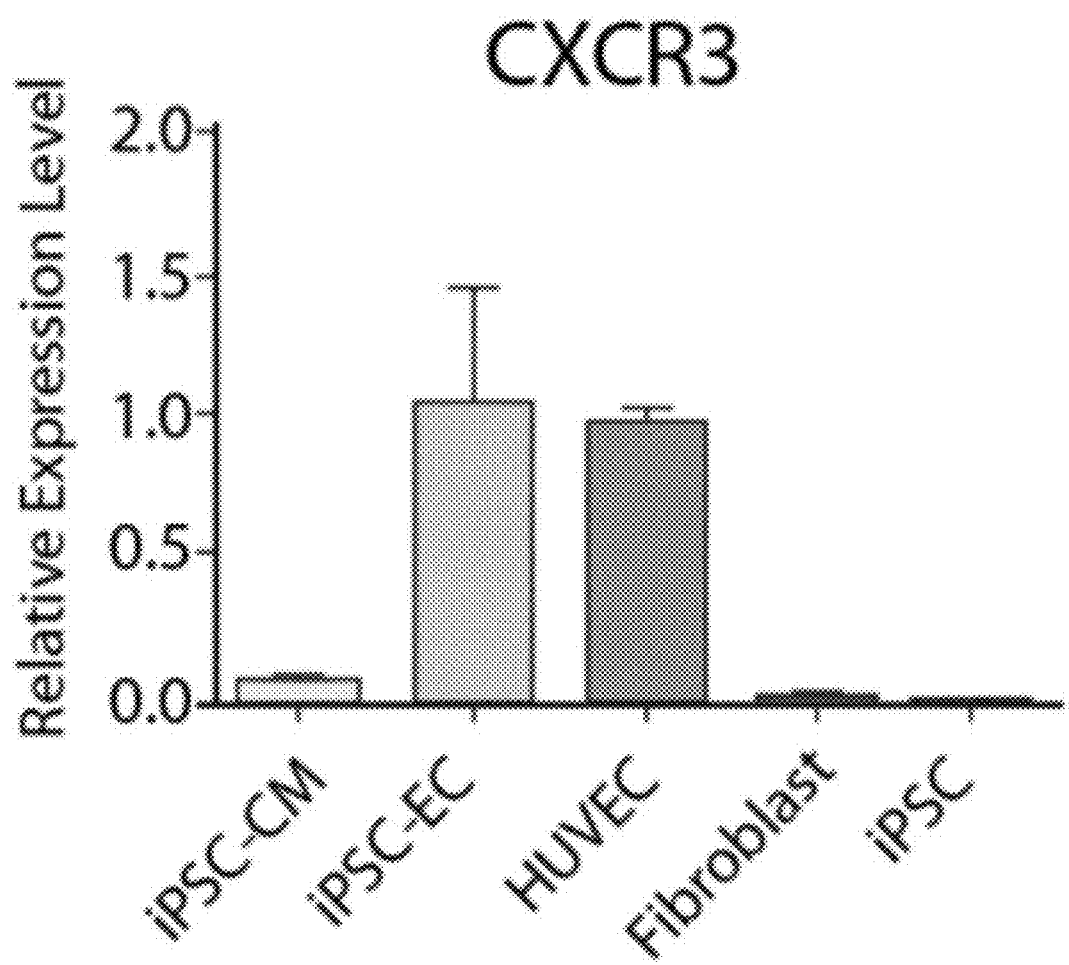
FIG. 5 is a bar graph showing the relative expression levels of CXCR3 in different cell types.

Elevated expression of CXCR3 is observed in hiPSC-ECs, HUVEC cells but not in other cell types (F) suggesting that the endothelium but not other cell subsets is a target of MIG and potentially other CXCR3 ligands as well. (See FIG. 5)

Example 6: MIG Impairs Endothelial Cell Function

Mouse thoracic aortas were carefully dissected, and vessels were cut into small rings and mounted on an isometric wire myograph chambers (Danish Myo Technology) and subjected to a normalization protocol. Following normalization, the vessels were incubated with either PBS or different concentrations of recombinant mouse MIG (R&D systems, catalog number 492-MM). A concentration-dependent contraction curve was created by accumulative application of the prostaglandin agonist U46619. Subsequently, concentration-dependent relaxation curves of Acetylcholine were conducted on these vessels and percent relaxation calculated for each dose.

Figure 6:
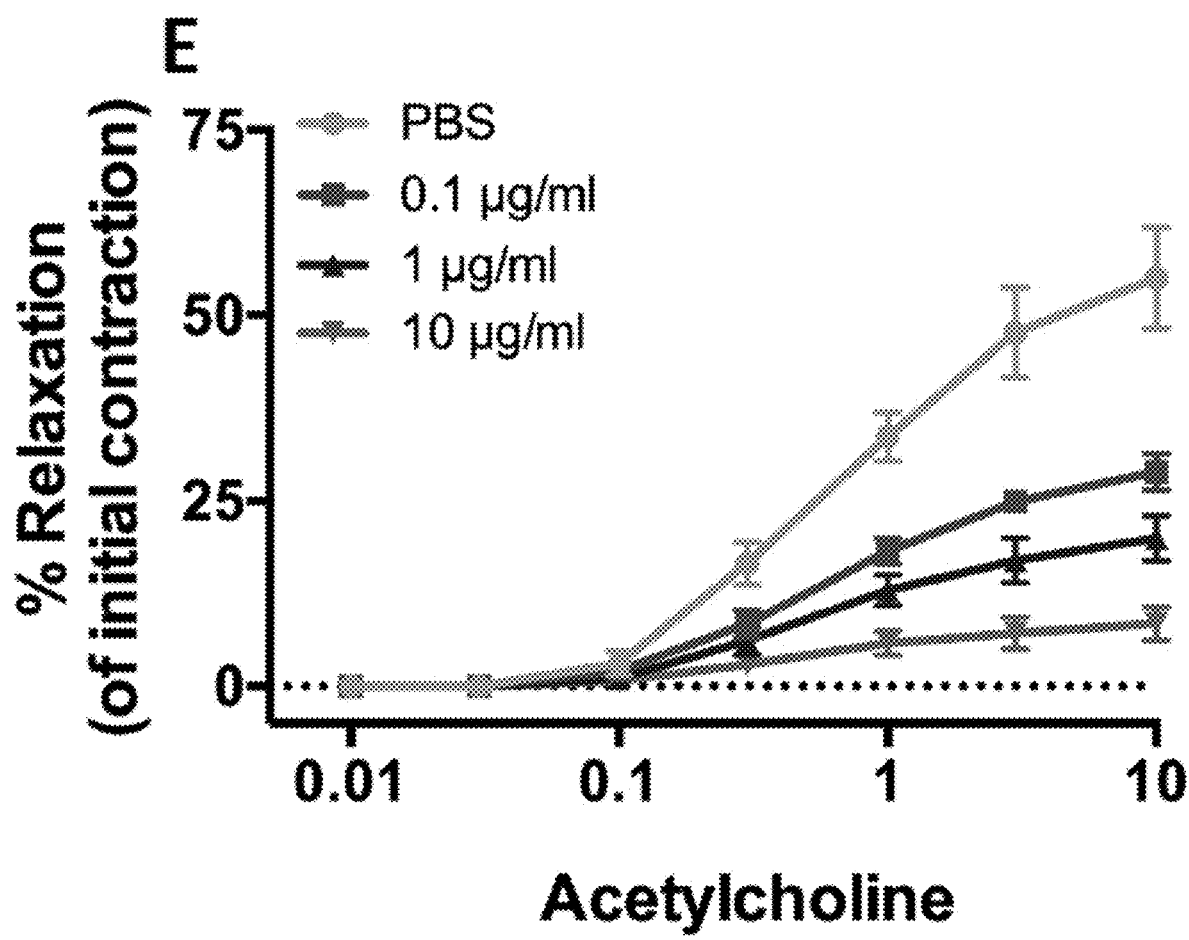
FIG. 6 depicts the percent relaxation of aorta cells in response to acetylcholine after exposure of the aorta cells to different levels of MIG.

FIG. 6 shows a line graph of percent relaxation of mouse thoracic aortic sections to Acetylcholine after exposure to different amounts of MIG. FIG. 6 shows impaired vascular reactivity with increasing concentrations of MIG. MIG causes a dose-dependent effect on vasorelaxation in treated aortas demonstrating that MIG impairs vascular function, and can contribute to arterial stiffness and premature aging of the cardiovascular system.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject asymptomatic for a cardiovascular disease, comprising the steps of: obtaining a single blood or a single serum sample from the subject; measuring a level of a plurality of cardiac markers in the blood sample or the serum sample, wherein the plurality of cardiac markers are selected from the group consisting of a MIG, a LIF and a SIRT3, wherein each of the MIG, the LIF and the SIRT3 are measured, wherein the MIG, the LIF and the SIRT3 are the only cardiac markers measured from the blood sample or the serum sample; selecting a subject with a level of the MIG outside of the lowest quintile for a chronological age of the subject; and administering an effective amount of an arsenic trioxide, a Roxarsone, or a humanized or fully human, full length anti-MIG IgG antibody for lowering the level of the MIG.

2. The method of claim 1, wherein the level of the MIG is outside of the lowest quartile.

3. The method of claim 1, wherein the level of the MIG is outside of the lowest tertile.

4. The method of claim 1, wherein the antibody has been modified with a protracting moiety.

* * * * *